US010351819B2

(12) United States Patent
Hribar et al.

(10) Patent No.: US 10,351,819 B2
(45) Date of Patent: Jul. 16, 2019

(54) METHOD FOR FABRICATION OF MICROWELLS FOR CONTROLLED FORMATION OF 3-DIMENSIONAL MULTICELLULAR-SHAPES

(71) Applicants: THE REGENTS OF THE UNIVERSITY OF CALIFORNIA, Oakland, CA (US); SANFORD BURNHAM PREBYS MEDICAL DISCOVERY INSTITUTE, La Jolla, CA (US)

(72) Inventors: Kolin C. Hribar, La Jolla, CA (US); Shaochen Chen, San Diego, CA (US); Darren Finlay, La Jolla, CA (US); Kristiina Vuori, La Jolla, CA (US); Xuanyi Ma, La Jolla, CA (US)

(73) Assignees: THE REGENTS OF THE UNIVERSITY OF CALIFORNIA, Oakland, CA (US); SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 53 days.

(21) Appl. No.: 15/511,429

(22) PCT Filed: Sep. 16, 2015

(86) PCT No.: PCT/US2015/050522
§ 371 (c)(1),
(2) Date: Mar. 15, 2017

(87) PCT Pub. No.: WO2016/044483
PCT Pub. Date: Mar. 24, 2016

(65) Prior Publication Data
US 2017/0283766 A1   Oct. 5, 2017

Related U.S. Application Data

(60) Provisional application No. 62/051,197, filed on Sep. 16, 2014.

(51) Int. Cl.
| | | |
|---|---|---|
| B29C 41/02 | (2006.01) |
| C12N 5/00 | (2006.01) |
| B29C 64/124 | (2017.01) |
| B29C 64/135 | (2017.01) |
| B01L 3/00 | (2006.01) |
| C12M 1/26 | (2006.01) |
| B33Y 10/00 | (2015.01) |
| C12M 1/32 | (2006.01) |
| C12M 1/00 | (2006.01) |
| C12N 5/09 | (2010.01) |

(Continued)

(52) U.S. Cl.
CPC .......... *C12N 5/0062* (2013.01); *B01L 3/5085* (2013.01); *B29C 64/124* (2017.08); *B29C 64/129* (2017.08); *B29C 64/135* (2017.08); *B33Y 10/00* (2014.12); *C12M 23/12* (2013.01); *C12M 23/22* (2013.01); *C12M 33/00* (2013.01); *C12N 5/0693* (2013.01); *C12N 5/0696* (2013.01); *B01L 2200/12* (2013.01); *B01L 2300/0819* (2013.01); *B01L 2300/0829* (2013.01); *B01L 2300/0858* (2013.01); *B01L 2300/0893* (2013.01); *C12N 2513/00* (2013.01); *C12N 2533/30* (2013.01)

(58) Field of Classification Search
CPC ... B29C 64/124; B29C 64/129; B29C 64/135; B29C 64/264; B29C 64/268; B29C 64/273; B29C 64/277; B29C 64/282; B29C 64/286
USPC .......................................... 264/401; 700/120
See application file for complete search history.

(56) References Cited

U.S. PATENT DOCUMENTS

| | | | | |
|---|---|---|---|---|
| 4,961,154 A | * | 10/1990 | Pomerantz | ............ B29C 64/129 264/401 |
| 5,545,367 A | | 8/1996 | Bae et al. | |
| 6,001,297 A | | 12/1999 | Partanen et al. | |

(Continued)

FOREIGN PATENT DOCUMENTS

| | | |
|---|---|---|
| CN | 102114275 B | 10/2012 |
| WO | 2012071477 A2 | 5/2012 |
| WO | 2014197622 A2 | 12/2014 |

OTHER PUBLICATIONS

Aldridge et al., "Human Mesenchymal Stem Cells are Recruited to Injured Liver in a ß1-Integrin and CD44 Dependent Manner," Hepatology, Sep. 2012, vol. 56, No. 3, pp. 1063-1073.

(Continued)

Primary Examiner — Leo B Tentoni
(74) Attorney, Agent, or Firm — Eleanor Musick; Musick Davison, LLP

(57) ABSTRACT

Using 3D printing, a microwell is formed by providing a plurality of masks, each mask representing a cross-section of a layer of the concave structure. Progressive movement of a projection plane exposes a pre-polymer solution to polymerizing radiation modulated by the masks to define the layers of the microwell, where each layer is exposed for a non-equal exposure period as determined by a non-linear factor. In a preferred embodiment, a first portion of the masks are base layer masks, which are exposed for a longer period than subsequent exposure periods. Shapes of the microwells, which may include circular, square, annular, or other geometric shapes, and their depths, are selected to promote aggregation behavior in the target cells, which may include tumor cells and stem cells.

20 Claims, 23 Drawing Sheets

(51) Int. Cl.
C12N 5/074 (2010.01)
B29C 64/129 (2017.01)

(56) References Cited

U.S. PATENT DOCUMENTS

| | | | |
|---|---|---|---|
| 7,219,016 B2 | 5/2007 | Rimm et al. | |
| 2002/0061472 A1 | 5/2002 | Cooper et al. | |
| 2005/0169962 A1 | 8/2005 | Bhatia et al. | |
| 2006/0100734 A1 | 5/2006 | Huang et al. | |
| 2007/0259156 A1 | 11/2007 | Kempers et al. | |
| 2008/0113293 A1 | 5/2008 | Shkolnik et al. | |
| 2010/0197013 A1 | 8/2010 | Kamp et al. | |
| 2011/0033887 A1 | 2/2011 | Fang et al. | |
| 2011/0086375 A1 | 4/2011 | Ungrin et al. | |
| 2011/0260365 A1 | 10/2011 | El-Siblani | |
| 2012/0216304 A1 | 8/2012 | Bhatia et al. | |
| 2012/0241740 A1 | 9/2012 | Park et al. | |
| 2013/0123988 A1* | 5/2013 | Jariwala | B29C 64/135 700/266 |
| 2013/0337066 A1 | 12/2013 | Zhang et al. | |
| 2013/0344601 A1* | 12/2013 | Soman | B29C 64/165 264/401 |
| 2014/0126239 A1 | 5/2014 | Huang et al. | |
| 2014/0193900 A1 | 7/2014 | Meyvantsson et al. | |
| 2016/0046072 A1* | 2/2016 | Rolland | B29C 64/124 264/401 |

OTHER PUBLICATIONS

Chen, Shaochen, "Advanced Laser Manufacturing of Polymeric Nanocomposites," Office of Naval Research YIP Grant No. N00014-04-1-0568 Final Project Report, The University of Texas at Austin, Jul. 2007, pp. 1-10.

Gauvin et al., "Microfabrication of complex porous tissue engineering scaffolds using 3D projection stereolithography," Biomaterials, May 2012, 33(15): 3824-3834.

Gou et al., "Bio-inspired detoxification using 3D-printed hydrogel nanocomposites," Nature Communications, May 8, 2014, 5:3774, pp. 1-9.

Hribar et al., "Light-assisted direct-wire of 3D functional biomaterials," Lab Chip, 2014, 14, pp. 268-275.

Ma et al., "Vesicular Polydiacetylene Sensor for Colorimetric Signaling of Bacterial Pore-Forming Toxin," American Chemical Society Journal, Jun. 11, 2005, vol. 21, No. 14, pp. 6123-6125.

PCT/US2015/050522—International Search Report and Written Opinion of the International Searching Authority dated Dec. 14, 2015, 9 pgs.

Soman et al., "A three-dimensional polymer scaffolding material exhibiting a zero Poisson's ratio," Soft Matter, 2012, 8, pp. 4946-4951.

Soman et al., "Digital microfabrication of user-defined 3D microstructures in cell-laden hydrogels," Biotechnology and Bioengineering, Jun. 3, 2013, vol. 110, No. 11, pp. 1-11.

Sullivan, et al., "Generation of Functional Human Hepatic Endoderm from Human iPS cells," Hepatology, Jan. 11, 2010, vol. 51, pp. 329-335.

Zorlutuna et al. "Microfabricated biomaterials for engineering 3D tissues," Advanced Materials, Mar. 13, 2012, vol. 24 No. 14, pp. 1782-1804.

Suri, S. Han et al., "Solid freeform fabrication of designer scaffolds of hyaluronic acid for nerve tissue engineering", Biomedical Microdevices, 2011, vol. 13(6), pp. 983-993.

* cited by examiner

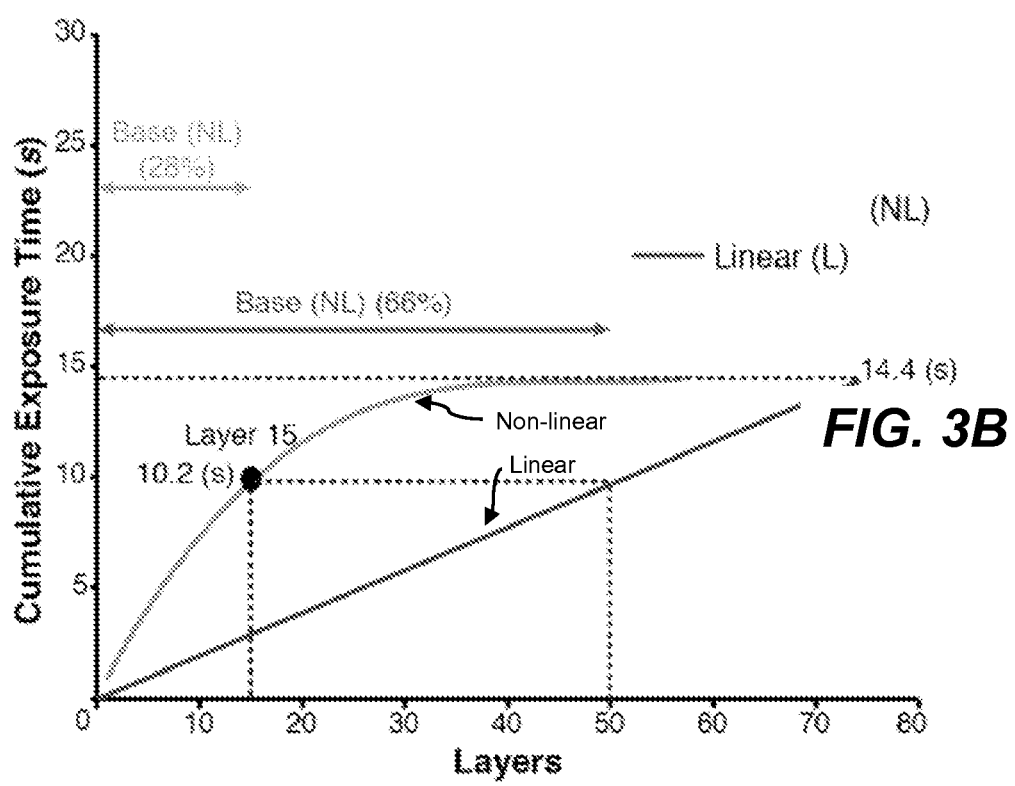

METHOD FOR FABRICATION OF MICROWELLS FOR CONTROLLED FORMATION OF 3-DIMENSIONAL MULTICELLULAR-SHAPES

RELATED APPLICATIONS

This application is a 371 national stage filing of International Application No. PCT/US2015/050522, filed Sep. 16, 2015, which claims the benefit of the priority of U.S. Application No. 62/051,197, filed Sep. 16, 2014, which is incorporated herein by reference in its entirety.

GOVERNMENT RIGHTS

This invention was made with government support under Grant No. EB012597 awarded by the National Institutes of Health and Grant No. CMMI-1120795 awarded by the National Science Foundation. The government has certain rights in the invention.

FIELD OF THE INVENTION

The present invention relates to a method and platform for 3D printing of microwells that can be configured to control aggregation and organoid generation into multicellular, 3-D shapes.

BACKGROUND OF THE INVENTION

In tissue engineering, cell biology, and the biomedical field at large, three-dimensional (3D) cell culture provides a tool to more accurately simulate the native in vivo environment for preclinical studies such as drug screening and cellular assays. Recent advances in 3D printing and fabrication technologies have, in turn, advanced the development of these 3D in vitro models. Spheroids, a staple of in vitro 3D culture, have long been employed in the formation and growth of embryoid bodies in embryogenesis, cell clustering for adult tissue growth and organogenesis, as well as cancer and liver organoid toxicity screening.

The ability to reproducibly generate multi-cellular spheroids is essential to provide an effective model of in vivo behavior. The hanging-drop method is a commercially available technique that has been extensively utilized in spheroid culture. This process is labor-intensive due to the need for spheroid transfer and sometimes lacks reproducibility. Micromolding and photolithography have been used to create microwells made of PDMS (polydimethylsiloxane), poly(ethylene glycol) (PEG), or agarose, however, these protocols frequently utilize harsh fabrication processes and produce microwells with limited optical transparency (requiring spheroid transfer for monitoring and imaging), generate multiple spheroids in the same well (in the case of flat wells), or lack control over spheroid placement within the well (making it difficult for high throughput imaging). One example of micro-molded wells for cell clustering is disclosed by Kugelmeier et al. in U.S. Pat. No. 8,911,690. The described well plates, which are available commercially under the name AggreWell™ (STEMCELL Technologies), are produced by one or more known mechanical and chemical processing techniques, such as molding, high-speed cutting, laser cutting, etching, etc. "Customization" of the sizes of the cavities for special applications is achieved through the use of filling inserts or dividers that are positioned when the wells are seeded. For practical reasons, these inserts typically have vertical sidewalls and, thus, modify the wall angles, making them less optimal for uniform cell aggregation.

While 3D spheroid culture are excellent tools for patterning and upscaling stem cell aggregates in a highly controlled manner, the dynamic changes in 3D shapes of the pluripotent stem cell (PSC) aggregates raise greater issues in understanding and controlling early embryogenesis stages. During early stages of embryogenesis in vivo, the PSC aggregates lose their circular symmetrical shapes and transform into polar and non-spherical structures, which then lead to the emergence of multiple different germ layers at separate regions. Such germ layer commitment is believed to be highly related to the 3D shapes of the PSC aggregates in addition to chemokine signaling. The ability to controlling the 3D PSC aggregate shapes in vitro would a powerful way to study the independent effects of shape and polarity on PSC lineage commitment.

Ideally, for cell aggregate culture, especially for screening purposes, the underlying material should consist of an optically clear substrate that encourages single 3D structure growth in the middle of the well, without the need for transfer to another plate, and limits protein deposition that could affect cell-cell attachment and spreading.

BRIEF SUMMARY

In an exemplary embodiment, a 3D printing platform is used to generate complex concavities in soft polymeric materials that guide the generation and development of reproducible multicellular clusters for 3D cell culture, while providing the optically-transparent subject required to monitor and image the development, without the need for transfer of the cluster to another surface. In one embodiment, a stereolithography machine is employed to pattern microwells of photopolymerizable biomaterials in various shapes and sizes configured to guide aggregation. Addition of cells to the pre-formed wells allows aggregation and organoid generation, the shapes and proportions of which can be controlled by well parameters. Multicellular spheroids and other three-dimensional shapes can be generated from various components and made to mimic the actual physiological state of primary biological material. Further the components can be manipulated for biological assessment.

The inventive approach is applicable to many areas of biomedical research, including (but not limited to) tissue engineering, drug screening, and cellular assays. Other applications include fabrication of contact or intraocular lenses, protein crystal growth methods (improving on hanging drop/sitting drop approaches), and formation of materials with tunable stiffness gradients.

In one aspect of the invention, a non-linear projection optical printing (nPOP) platform uses variable baseline UV exposure to fabricate concave hydrogel microstructures that can be used in 3D cell culture (e.g., spheroid formation). Compared to other fabrication technologies such as micromolding, nPOP can reproducibly generate any concave shape or design within seconds. Baseline exposure during fabrication is an important component of the integrity of the gel's micro-architecture and resulting spheroid culture. In a biologically-relevant context, the 3D printed poly(ethylene glycol) (PEG) microwells offer the optimal combination of a non-adhering surface that promotes 3D cell culture, which is optically clear and can generate single spheroids in the center of the well. The size of the spheroids is dictated by the seeding density alone due to their controlled concavity.

According to one aspect of the invention, a method for three-dimensional printing of a concave structure comprises providing a plurality of masks, each mask representing a cross-section of a layer of the concave structure; and progressively moving a projection plane to expose a pre-polymer solution to a polymerizing radiation source modulated by the plurality of masks to define the plurality of layers of the concave structure, wherein each layer is exposed for an exposure period within a total exposure time, wherein the exposure periods are non-equal portions of the total exposure time. In a preferred embodiment, a first portion of the plurality of masks comprises base layer masks, wherein a first exposure period for the first portion is longer than subsequent exposure periods. The total exposure time may be determined according to the relationship $T_0+T_0*(1+L_i*A_2)^2$, where $T_0$ is the first exposure period, $L_i$ is a layer number of a layer of the plurality of layers, and $A_2$ is a non-linear factor. The non-linear factor $A_2$ may be within a range of −0.025 to 0, the first exposure period $T_0$ may be within a range of 0.5 second to 1 second and the total exposure time is within a range of 10 seconds to 30 seconds. In a particularly preferred embodiment, the non-linear factor $A_2$ is −0.023 and the first exposure period $T_0$ is 0.95. In most embodiments, the pre-polymer solution is PEGDA. Other materials that may be used include GelMA (gelatin methacrylate), HA (hyaluronic acid), and other hydrogels and polymers that exhibit the qualities needed for cell culture.

The step of progressively moving a projection plane comprises moving a stage supporting a container containing the pre-polymer solution along a z-axis relative to the polymerizing radiation source. In a preferred embodiment, the stage is moved at non-equal time increments corresponding to the exposure periods.

The plurality of masks is configured for defining to an array of circular patterns of progressively increasing diameter from a bottom of the concave structure to a top of the concave structure. A first portion of the plurality of masks has no pattern, so that the entire pre-polymer solution is exposed to polymerizing radiation.

According to another aspect of the invention, a microwell configured for controlled spheroid formation comprises a concave polymer structure formed by progressively moving a projection plane to expose a pre-polymer solution to a polymerizing radiation source modulated by a plurality of masks to define the plurality of layers of the concave structure, wherein each layer is exposed for an exposure period within a total exposure time, wherein the exposure periods are non-equal portions of the total exposure time. In a preferred embodiment, a first portion of the plurality of masks comprises base layer masks, wherein a first exposure period for the first portion is longer than subsequent exposure periods. The total exposure time may be determined according to the relationship $T_0+T_0*(1+L_i*A_2)^2$, where $T_0$ is the first exposure period, $L_i$ is a layer number of a layer of the plurality of layers, and $A_2$ is a non-linear factor. The non-linear factor $A_2$ may be within a range of −0.025 to 0, the first exposure period $T_0$ may be within a range of 0.5 second to 1 second and the total exposure time is within a range of 10 seconds to 30 seconds. In a particularly preferred embodiment, the non-linear factor $A_2$ is −0.023 and the first exposure period $T_0$ is 0.95. In most embodiments, the pre-polymer solution is PEGDA.

The step of progressively moving a projection plane comprises moving a stage supporting a container containing the pre-polymer solution along a z-axis relative to the polymerizing radiation source. In a preferred embodiment, the stage is moved at non-equal time increments corresponding to the exposure periods.

In an exemplary embodiment, a plurality of masks is configured for defining to an array of circular patterns of progressively increasing diameter from a bottom of the concave structure to a top of the concave structure. A first portion of the plurality of masks has no pattern, so that the entire pre-polymer solution is exposed to polymerizing radiation. 24. The microwell of claim 14, wherein a first portion of the plurality of masks comprises no pattern, so that the entire pre-polymer solution is exposed to polymerizing radiation.

In another embodiment, the masks are configured to define arrays of circular, square and annular patterns for purposes of controlling the 3D shapes of iPSC and embryonic stem cell aggregates, to promote the development of polarity and differentiation into germ layers.

nPOP employs non-linear UV light exposure to precisely print photocrosslinkable PEG microwells with any concave shape and gradient design. For biological relevance, the microwells demonstrate optical clarity for imaging purposes and generate single multicellular spheroids and other 3D shapes in the middle of each well. BT474 breast cancer cells as well as human induced pluripotent stem cells (iPSCs) have been used to generate tumor spheroids and embryoid bodies (EBs), respectively. The 3D shapes are grown on a microwell array—one cluster per well—for ease of analysis and imaging. Importantly, cluster size can be controlled by adjusting the cell density alone. In this study, we varied the size of the tumor clusters from 150-350 μm in diameter. Above the critical size of 200-250 μm in diameter, cancer spheroids have a demonstrated chemical gradient and oxygen gradient, potentiating a hypoxic and sometimes necrotic core that is more representative of the tumor microenvironment in vivo. Additionally, EBs of variable sizes have shown distinct differentiation patterns, and thus the need to create a platform for generating EBs with controlled sizes. This inventive application of nPOP technology can greatly enhance tissue engineering and drug screening fields in the generation and imaging of 3D multicellular clusters and has broad implications in future non-linear 3D printing technologies.

BRIEF DESCRIPTION OF THE DRAWINGS

FIG. 3B is a plot of progression of exposure time over layers, with linear and non-linear regimens compared.

FIG. 4B is a plot showing spheroid sizes quantified over 10 days for each cell seeding density. The inset provides percent change in spheroid size in relation to the previous time point.

DETAILED DESCRIPTION

The proposed 3D printing technology utilizes continuous 3D printing of a series of layers using an automated stage. While similar 3D printing systems have been previously disclosed (see, e.g., International Publication No. WO2014/197622, and International Publication No. WO2012/071477, which are incorporated herein by reference), the present invention provides an important modification that uses non-linear UV light exposure, i.e., non-linear projection optical printing (nPOP), to enable precise control of the polymerization for formation of optimal structures for cell culture.

According to the exemplary embodiments, a method for three-dimensional printing of a concave structure comprises providing a plurality of masks, each mask representing a cross-section of a layer of the concave structure. Progressively moving a projection plane exposes a pre-polymer solution to a polymerizing radiation source modulated by the plurality of masks to define the plurality of layers of the concave structure, wherein each layer is exposed for an exposure period within a total exposure time, wherein the exposure periods are non-equal portions of the total exposure time as determined by a non-linear factor. In a preferred embodiment, a first portion of the plurality of masks comprises base layer masks, wherein a first exposure period for the first portion is longer than subsequent exposure periods.

Figure 1A:
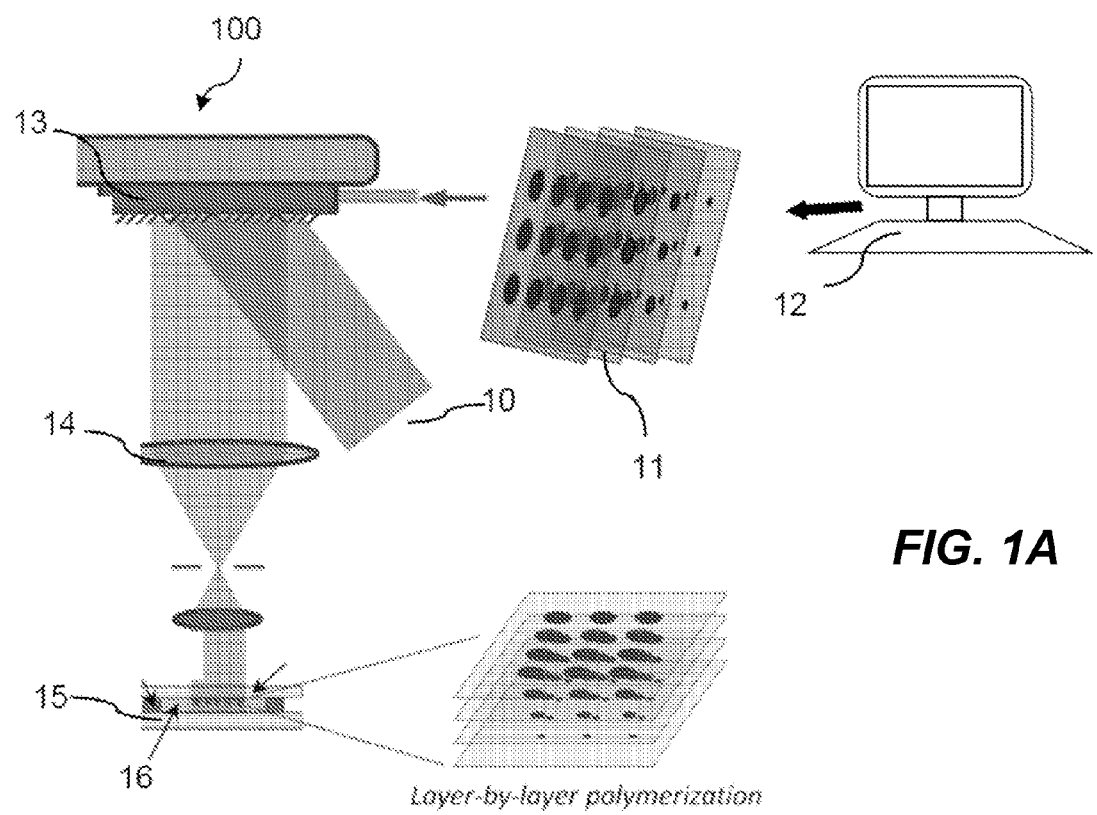
FIG. 1A is a schematic diagram of an embodiment of the nPOP 3D printing system.

The basic elements of a 3D printing platform 100 for use in an exemplary embodiment of the invention are illustrated in FIG. 1A: a UV light source 10, a computer controller/processor 12, which performs sliced image-flow generation, i.e., "virtual masks" 11, and system synchronization, a digital micromirror device (DMD) chip 13 for optical pattern generation, a projection optics assembly 14, and an multi-axis stage 15 for sample position control. The DMD chip 13, formed from approximately one million micromirrors, modulates the UV light and projects an optical pattern generated via computer 12 based on a custom-designed computer-aided design (CAD) model onto the photopolymer solution. The optical pattern is projected through optical lenses 14 and onto the photosensitive material 16 to fabricate a 3D polymer structure. Complex 3D structures can be fabricated through a continuous, layer-by-layer polymerization process that is synchronically controlled using a motorized multi-axis stage 15.

An appropriate UV light source 10 for use in the nPOP system can be selected from different sources including a laser (CW or pulsed), mercury bulb (arc lamp), and an LED source, which may include an array of LEDs emitting at one wavelength or across a range of UV wavelengths. In an exemplary embodiment, a pulse mode-locked femtosecond laser may be used. The light source 10 may include controllable parameters, responsive to the computer controller/processor 12, including intensity, iris, aperture, exposure time, shutter, and wavelength. Selection of appropriate operating parameter will depend on the materials used and the desired characteristics of the scaffold and will be within the level of skill in the art.

As an alternative to the DMD chip, a galvanometer optical scanner or a polygon scanning mirror, may be used. Both of these technologies, which are commercially available, are known in their application to high speed scanning confocal microscopy. Selection of an appropriate scanning mechanism for use in conjunction with the inventive system and method will be within the level of skill in the art.

Figure 1B:
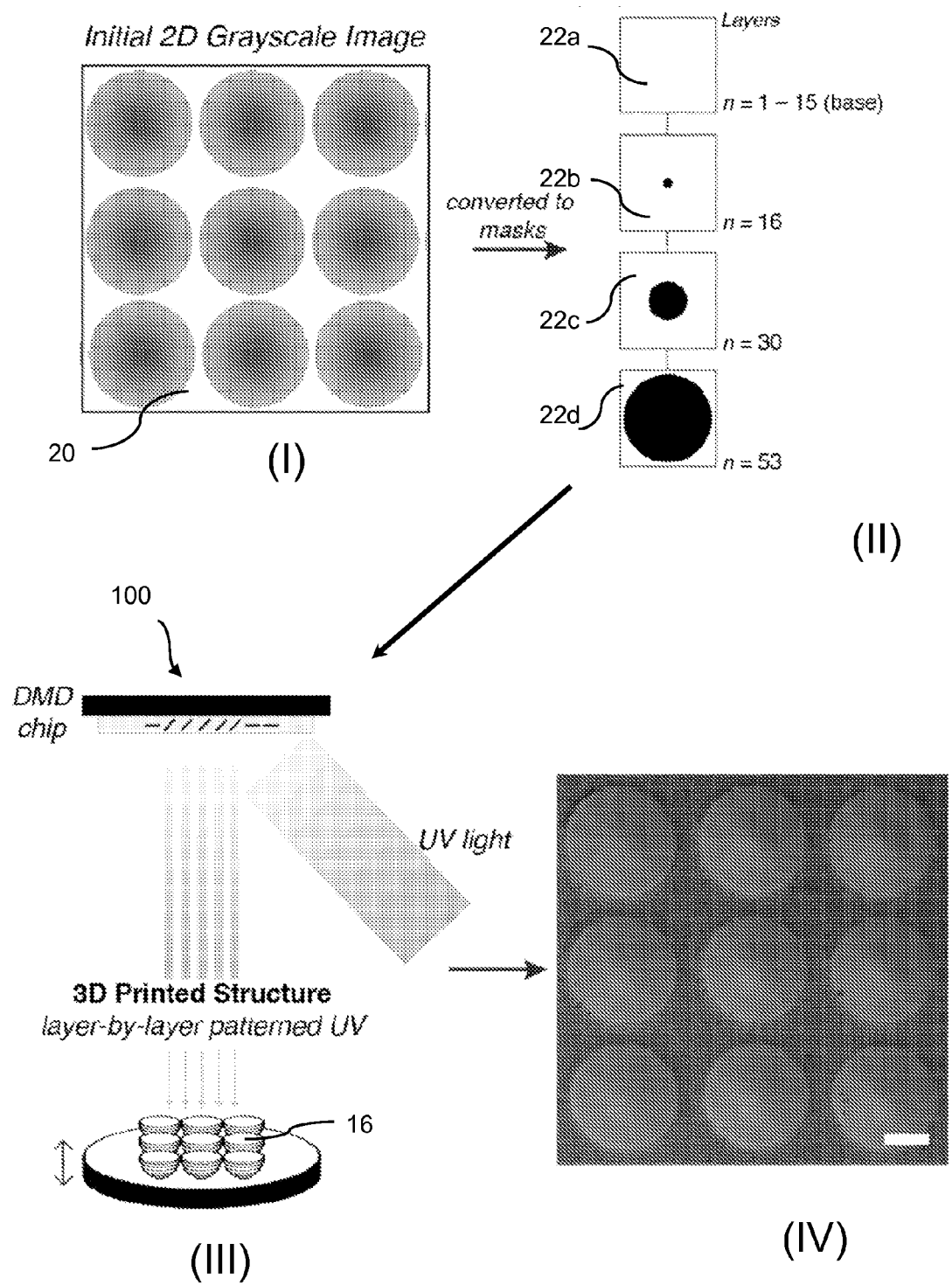
FIG. 1B illustrates an exemplary process sequence for generating 3D printed microwells according to an embodiment of the invention.

As shown in FIG. 1B, a two-dimensional computer-generated image 20 (Panel (I)) is converted into a series of layer slices based on its grayscale intensity. The gradient pattern was designed using ADOBE® PHOTOSHOP® converted to a grayscale image. The image was then processed through in-house software and z-sliced into a series of transverse planes, according to the grayscale intensity of each pixel.

Panel II of FIG. 1B provides a few examples of simple masks, where the white areas of the masks 22a-22d correspond to UV exposure and black areas block UV light transmission so that no exposure occurs. Each digital mask layer represents a cross-sectional image in the series of layer slices in proportion to the height of the structure (in this case 500 μm). The series of masks is input into the computer processor/controller of the nPOP system 100 (Panel III) for controlling the digital micromirror device (DMD) 100 for UV projection onto the photocurable material 16 in a container located on the automated stage. The resulting 3D microwell structure for the initial grayscale image of Panel I is shown in the SEM micrograph in Panel IV.

Figure 1C:
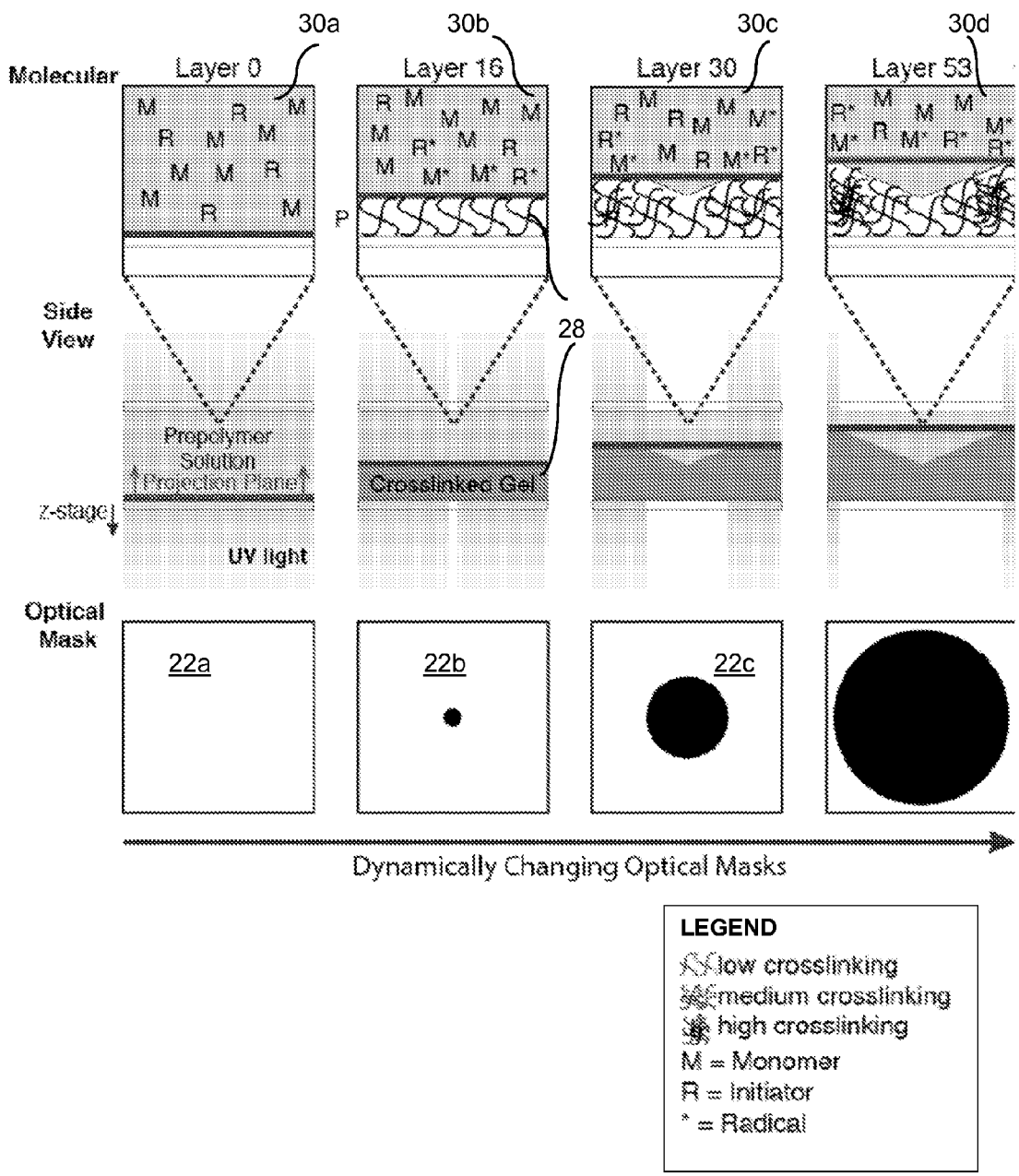
FIG. 1C is a series of schematic diagrams illustrating an exemplary printing sequence.

In the described embodiment, we used a circular microwell pattern (500 μm in diameter) with a gradient pattern and applied 53 layers to the image. FIG. 1C schematically illustrates an exemplary nPOP process as it progresses through the optical mask layers. For the first number of layers or masks (in this example, 15 layers), UV light was projected onto the entire prepolymer solution 16, photocrosslinking the base of the microwell structure. The upper mask in Panel II of FIG. 1B is used for projection of the base structure. Subsequent optical masks with increasing areas of non-exposure (black areas, as indicated in Panel (II) of FIG. 1B) are displayed on the DMD to control exposure of the following layers. Continuing the example of FIG. 1B, Panel (II), the second number of layers, beginning with layer n=16, is shown as a small dot. At layer n=30, a larger dot is shown, progressing up to the largest dot at uppermost layer n=53.

FIG. 1C provides a different perspective of the processing with the same example optical masks 22a-22d. The boxes 30a-30d at the upper portion of each "frame" indicate the molecular components of the prepolymer solution at the given stage in the process, where "M" indicates monomer, "R" indicates initiator, and "*" indicates radical. In the first frame (layer 0), light is projected through mask 22a into the prepolymer solution to define the base structure 28. The z-stage moves downward, shifting the projection plane upward. As indicated by box 30b, a low degree of crosslinking has occurred in the base structure as the sequence progresses to layer 16. At this point, mask 22b is used to project partially-blocked UV light into the prepolymer solution. As shown by box 30c, crosslinking within the base structure continues while the lower dimensions of the microwell are defined. As the process reaches layer 53, a high degree of crosslinking is present near the outer edges, and the inner, blocked areas of defined.

The microwell is built in a continuous layer-by-layer fashion, alongside a continuously moving z-stage that coordinates its movements in the z direction with changes in the optical masks. The layer numbers and relative blocking mask shapes and sizes are provided as examples only. In addition to circles, mask shapes (and the microwells printed therefrom) may also include oval, square, rectangular, annular (ring), polygonal, and other geometric shapes depending on the desired aggregation behavior. It will be readily apparent to those in the art that selection of shapes, the number of the layers and progression of blocking mask dimensions will depend on parameters appropriate for the intended application.

Figure 1D:
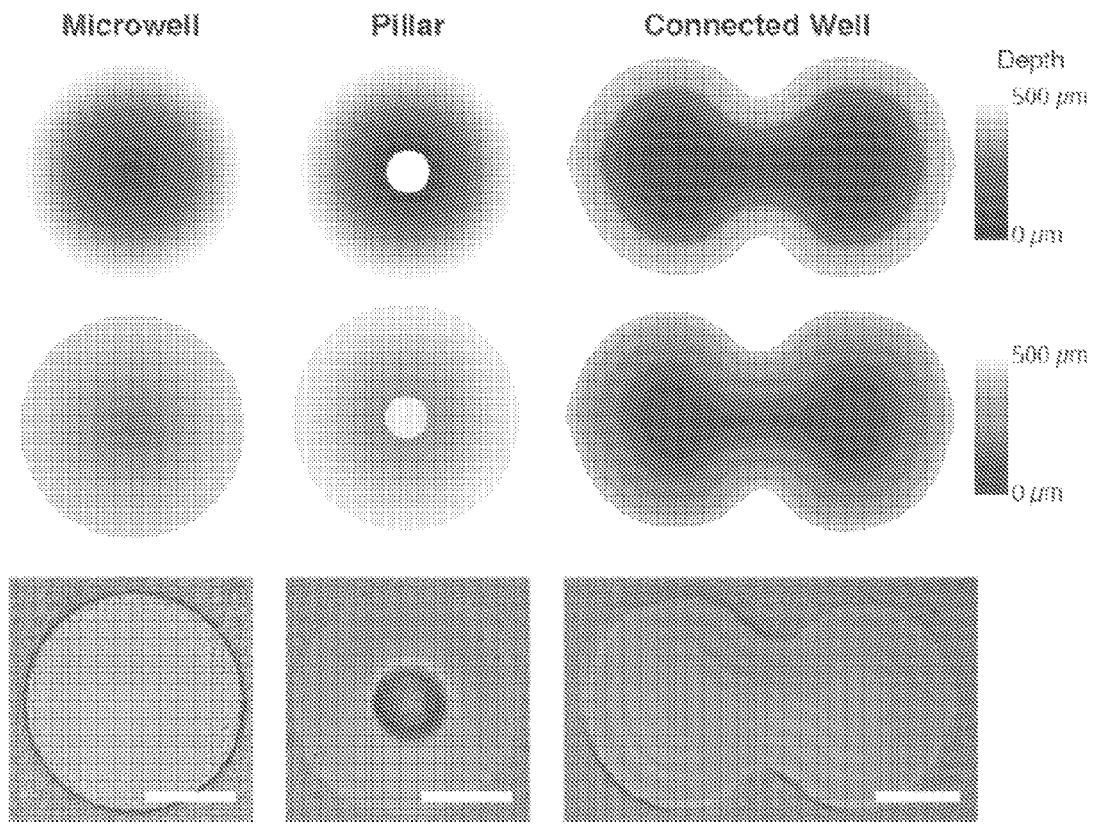
FIG. 1D illustrates sample gradient patterns and the resulting 3D printed structures generated using an embodiment of the nPOP platform.
Figure 1E:
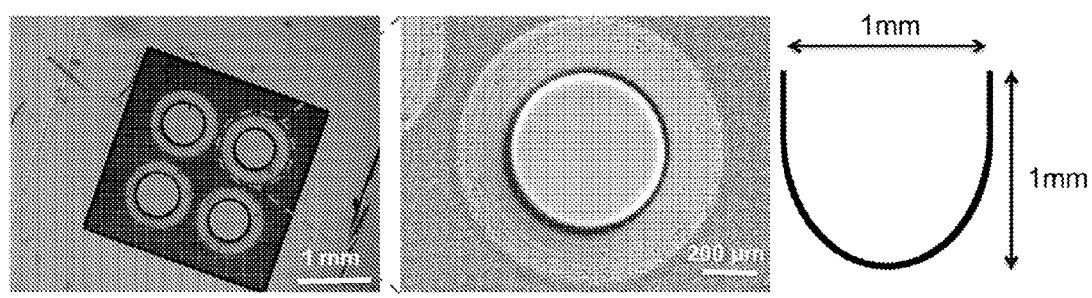
FIG. 1E shows SEM micrographs of microwells fabricated using the inventive platform and method with the profile and nominal dimensions for a well.

Setting the z-height to 500 μm, for the example of 53 layers, the stage moves 9.4 μm for each layer, continuously changing the projection plane within the prepolymer solution as it moves through the layering sequence. Importantly, the nPOP technology permits the creation of any complex and precisely-defined concave structure simply by changing the design or gradient of the input pattern. A few examples of these designs are provided in FIG. 1D. From left to right, the designs shown are a microwell, a pillar and a pair of connected wells. From top to bottom, the images show a gradient pattern, the same design in grayscale, and micrographs of the resulting 3D printed structure. This represents a major advancement to previously-reported 3D printing platforms, which rely on printing one dot and then one layer at a time, while overcoming limitations associated with micromolding of soft biomaterials with complex designs. FIG. 1E provides SEM micrographs of microwells fabricated using the inventive platform and method. The right panel of FIG. 1E shows the profile and nominal dimensions of each microwell.

Evaluation of the microwells included SEM images of the samples. In each case, preparation of the microwell samples for SEM imaging involved freeze-drying the samples in a glass vial exposed to isopropanol in dry ice, and lyophilizing overnight. Samples were then coated with iridium and imaged using an FEI SFEG Ultra-high resolution SEM.

In a preferred embodiment, the prepolymer solution used to fabricate the microwells is 20% (w/v) poly(ethylene glycol) (PEG) diacrylate (DA). PEG is an FDA-approved biomaterial and often utilized in cell culture because of its many useful qualities for biomedical applications, including low immunogenicity, high water retention, biocompatibility, minimal protein adsorption, tunability, and optical clarity. An additional advantage of this material selection is that PEG acts as a non-adhering material, thus assisting in the limitation of cell-material interaction and promoting cell clustering. Other materials that may be used include GelMA (gelatin methacrylate), HA (hyaluronic acid), and other hydrogels and polymers that exhibit the qualities needed for cell culture.

For testing, (PEGDA) (MW 700, Sigma), 0.05% Irgacure 2959 (Ciba) in phosphate buffer saline (PBS) was administered between two glass slides and exposed to 15 mW/cm2 UV light source (Omnicure S2000, 365 nm) using dynamic optical projection stereolithography setup.

UV photopolymerization and gelation of PEGDA is a non-linear process, where free radical initiation, polymer chain propagation, and termination take place on multi-order kinetics. Thus, the 3D printing process according to one embodiment of the invention allows for nonlinear UV exposure. In our layer-by-layer nPOP fabrication setup, non-linear UV exposure for a series of layers is controlled by the following equation:

$$\text{Total exposure time } (T_{total}) = T_0 + T_0 * (1 + L_i * A_2)^2, \quad (1)$$

where $T_0$ is the exposure time for the base layer, $L_i$ is the layer number, and $A_2$ is the non-linear factor. Total exposure time is the aggregate exposure for all the layers. For purposes of this evaluation, to build a microwell of about 1 mm in both depth and upper diameter, we looked at total exposure times within a range of about 10 seconds to 30 seconds, base layer exposure times within a range of around 0.5 to 1 second, with a non-linear factor $A_2$ within a range of about −0.025 to 0.

Based on the exposure time and selected height, the software adjusts the speed of the automated stage. For initial testing, the z-height for all structures was held constant at 500 μm. Microwells were polymerized onto glass coverslips pretreated with the chemical modification of 3-(Trimethoxysilyl)-Propyl Methacrylate (TMSPMA). After fabrication, the microwells were washed three times in PBS over the course of two days.

Figure 2A:
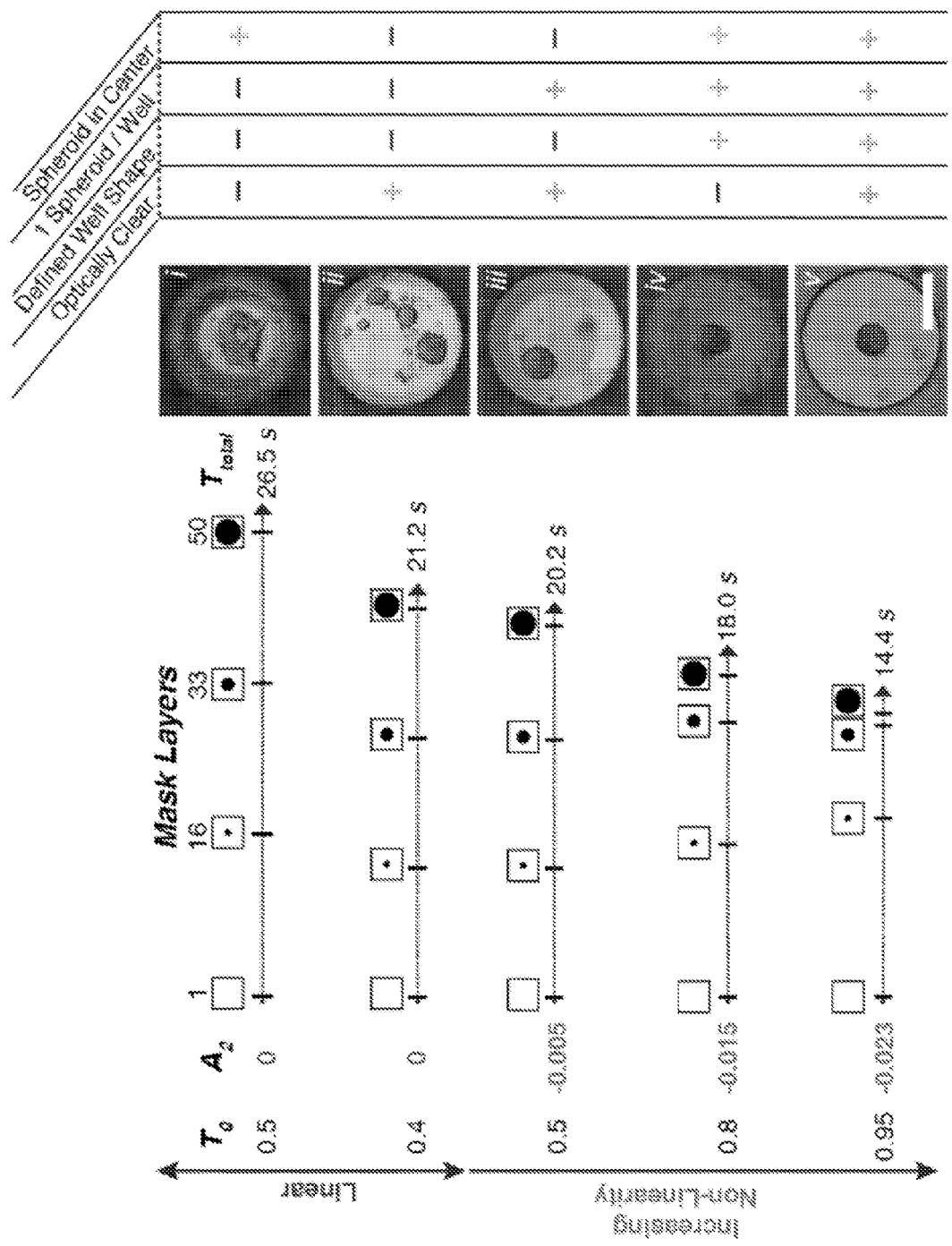
FIG. 2A provides a schematic example of how variation in the microwell fabrication parameters ($T_0$ and non-linear factor, $A_2$) affects spheroid growth within the fabricated well. SEMs of the resulting microwells and day 2 spheroid culture are shown on the right (fourth column) (scale bars=200 μm.)

FIG. 2A provides a schematic illustration of how selection of the fabrication parameters of Equation (1) can impact the resulting structure, even when keeping the mask design constant.

The horizontal arrows in each of the five panels (i-v) correspond to exposure time from left to right. The vertical arrows compares initial exposure time $T_0$ for the base layer. At lower values of $T_0$, e.g., panels i and ii of FIG. 2A, the well shape becomes wider and less polymerized, and is largely unpolymerized in the middle of the well. This lack of polymerization is presumably the result of a lower exposure time for the base layers (15 layers in the illustrative example), during which the entire prepolymer solution is exposed to UV light. Without wishing to be bound by theory, we hypothesize that a longer exposure time to the base layers is needed to generate free radicals for the rest of the structure. While increasing exposure to the base layers can be achieved by increasing $T_0$ in a linear fashion, this approach has the effect of overpolymerizing the remaining layers of the microwell structure, which can lead to an undefined well shape that is not optically clear, as indicated in panel i of FIG. 2A. As a result, we can modulate the non-linear factor, $A_2$, to vary the exposure time for each layer. When $A_2$ is negative, each successive layer is exposed for a shorter duration, in turn speeding up the entire fabrication process as it proceeds through the 53 layers. As shown in FIG. 2A, where panels iii to v decrease in total exposure time from 20.2 seconds to 14.4 second, respectively. By increasing $T_0$ and making $A_2$ more negative (shown in the second column of the figure), the bulk of the UV exposure shifts to the earlier layers, thus allowing more time for free radical generation in the base layers, during which the entire prepolymer solution is exposed to UV light. Column 5 of FIG. 2A provides a table summarizing the qualitative microwell characteristics obtained through variation of the processing parameters ($T_0$ and $A_2$) in the illustrated examples of panels i to v. The microwells formed using the parameters of panel i, with $T_0=0.5$ and $A_2=0$, exhibited poor optical clarity and shape definition, and did not promote formation of a single spheroid, although what was formed was well-centered. The micrograph in the fourth column of the figure shows an example of 2 day spheroid formation for the microwells of panel i. Microwells fabricated using the parameters of panel ii, with $T_0=0.4$ and $A_2=0$, exhibited good optical clarity, but had poor shape definition and did not promote formation of a single, centered spheroid. The parameters of panel iii, with $T_0=0.5$ and $A_2=-0.005$, produced microwells that exhibited good optical clarity and promoted formation (at 2 days) of a single spheroid, but had poor shape definition and the spheroid was not centered, as shown in the micrograph for panel iii. The parameters of panel iv, with $T_0=0.8$ and $A_2=-0.015$, produced microwells with poor optical clarity but which were well defined and promoted formation of a single, centered spheroid, as shown in the micrograph for panel iv. Based on these results, we empirically determined the optimal $T_0$ and $A_2$ values ($T_0=0.95$; $A_2=-0.023$) to make an optically clear microwell that could generate a single 3D cluster in the center of the well, the results of which are shown in panel v.

Figure 2B:
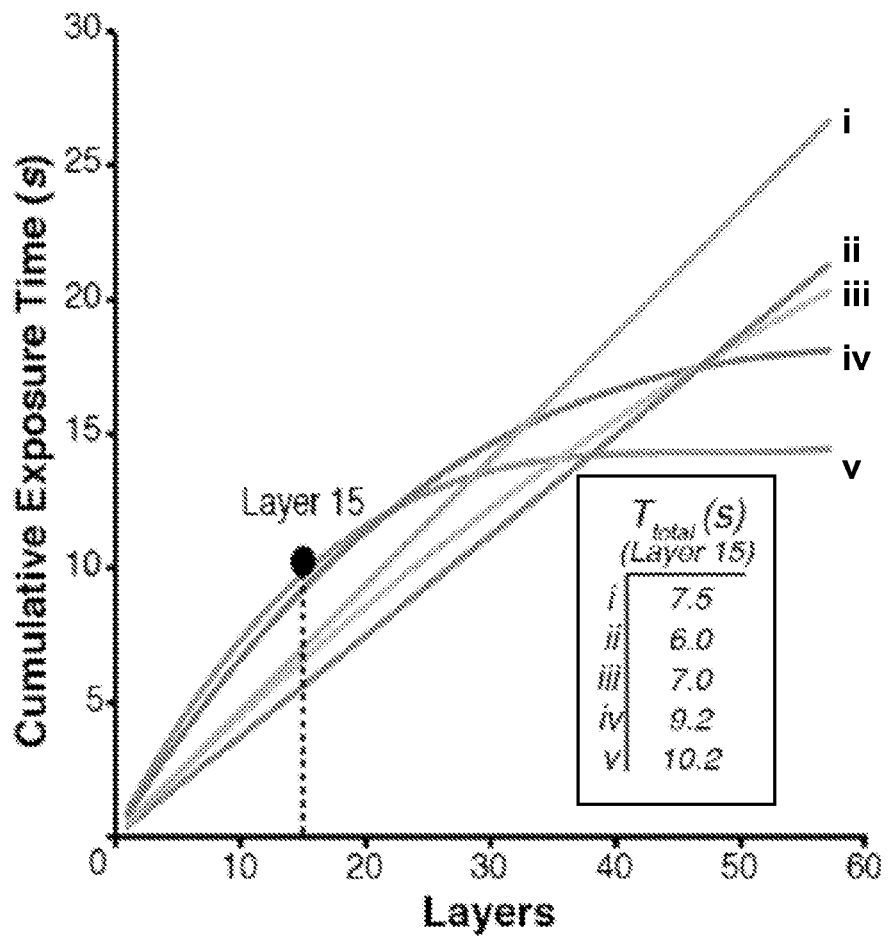
FIG. 2B is a plot of cumulative total exposure time at different layers in the optical mask series. Total values at layer 15 are displayed in the inset.

FIG. 2B provides a graphical understanding of the cumulative exposure time in accordance to the layers for each of the five cases (i to v) shown in FIG. 2A. It is interesting to note the cumulative exposure time for the first 15 base layers increases from 6.0 seconds for linear exposure to 10.2 seconds for non-linear exposure in panels ii and v of FIG. 2A, respectively, as indicated in the FIG. 2B inset. Thus, we believe that a longer exposure time period for the base layers is required to initiate the free radical polymerization process throughout the prepolymer solution. Below this time, we observed unpolymerized sections in the microwell center.

Figure 2C:
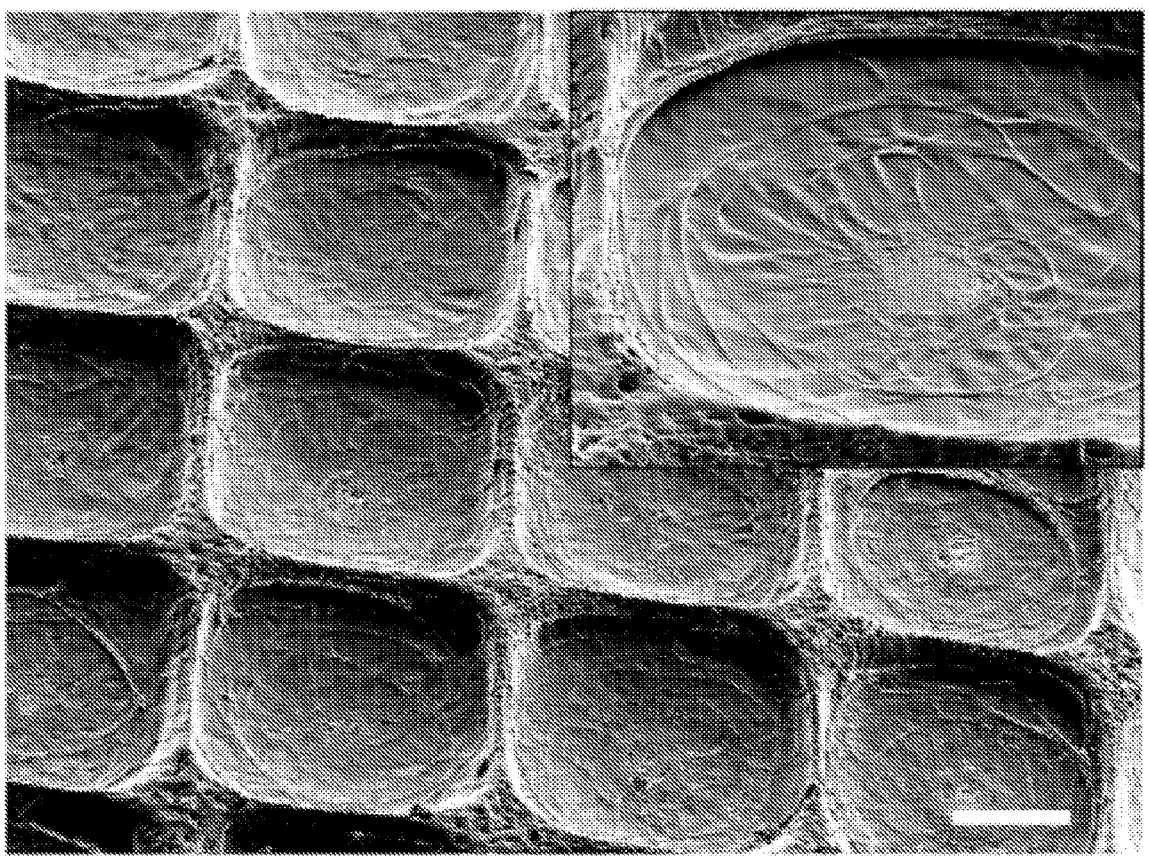
FIG. 2C is a SEM micrograph comparing different gradient patterns to flat microwells, and the resulting 3D cell culture is shown. Scale bars=200 μm

After optimizing the fabrication parameters, microwells with $T_0$ and $A_2$ values of 0.95 seconds and −0.023, respectively (total exposure time ~14.4 s) were used for the remainder of the experiments. Scanning electron microscopy was used to confirm the 3D shape of the microwells, shown in FIG. 2C, wherein the scale bar is 200 µm. Each microwell displays a gradually increasing slope from the center to the edge and steep walls, indicating a concave shape.

Figure 2D:
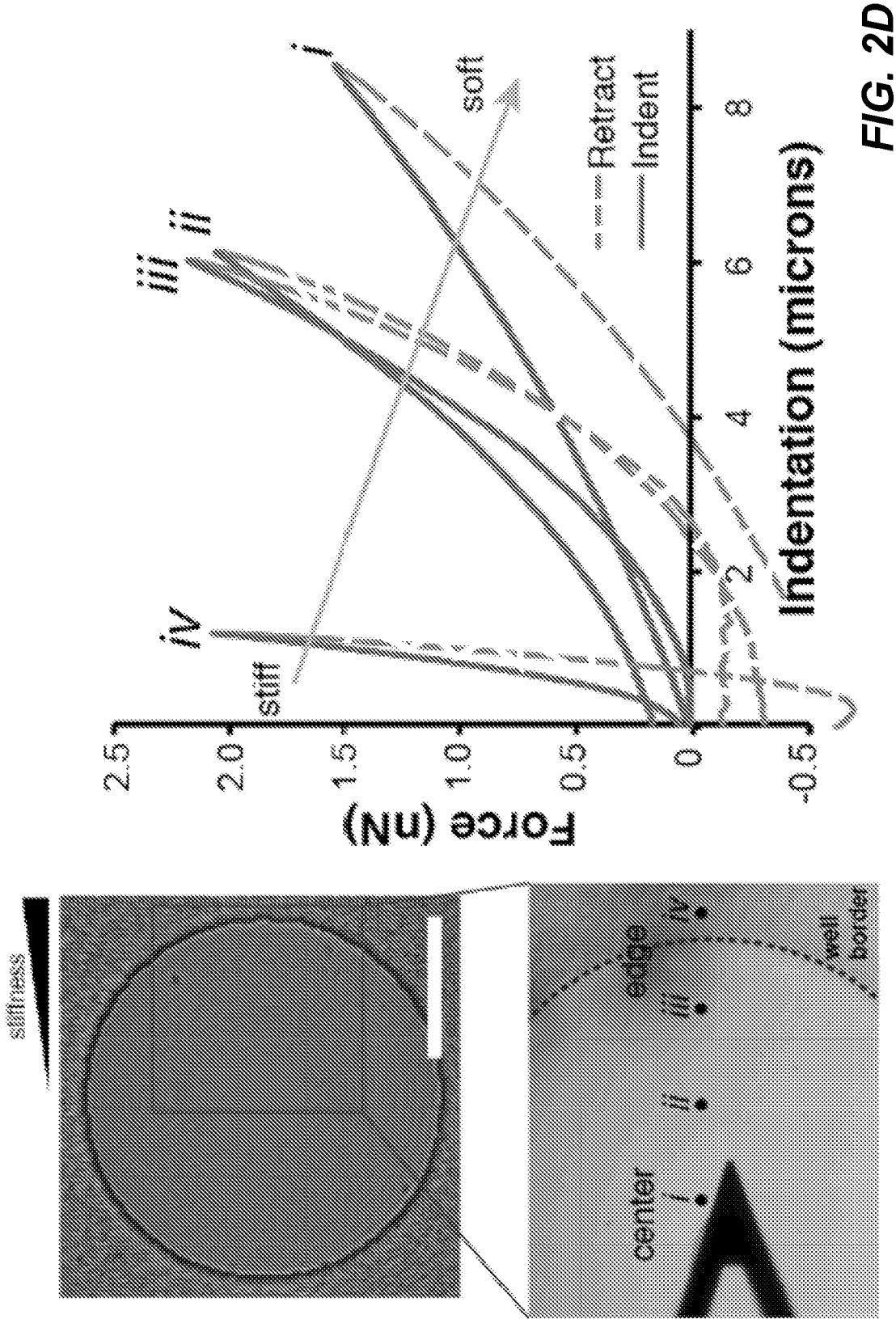
FIG. 2D is a plot of AFM stiffness results at different regions of the microwell. (Scale bars=200 μm.)
Figure 2E:
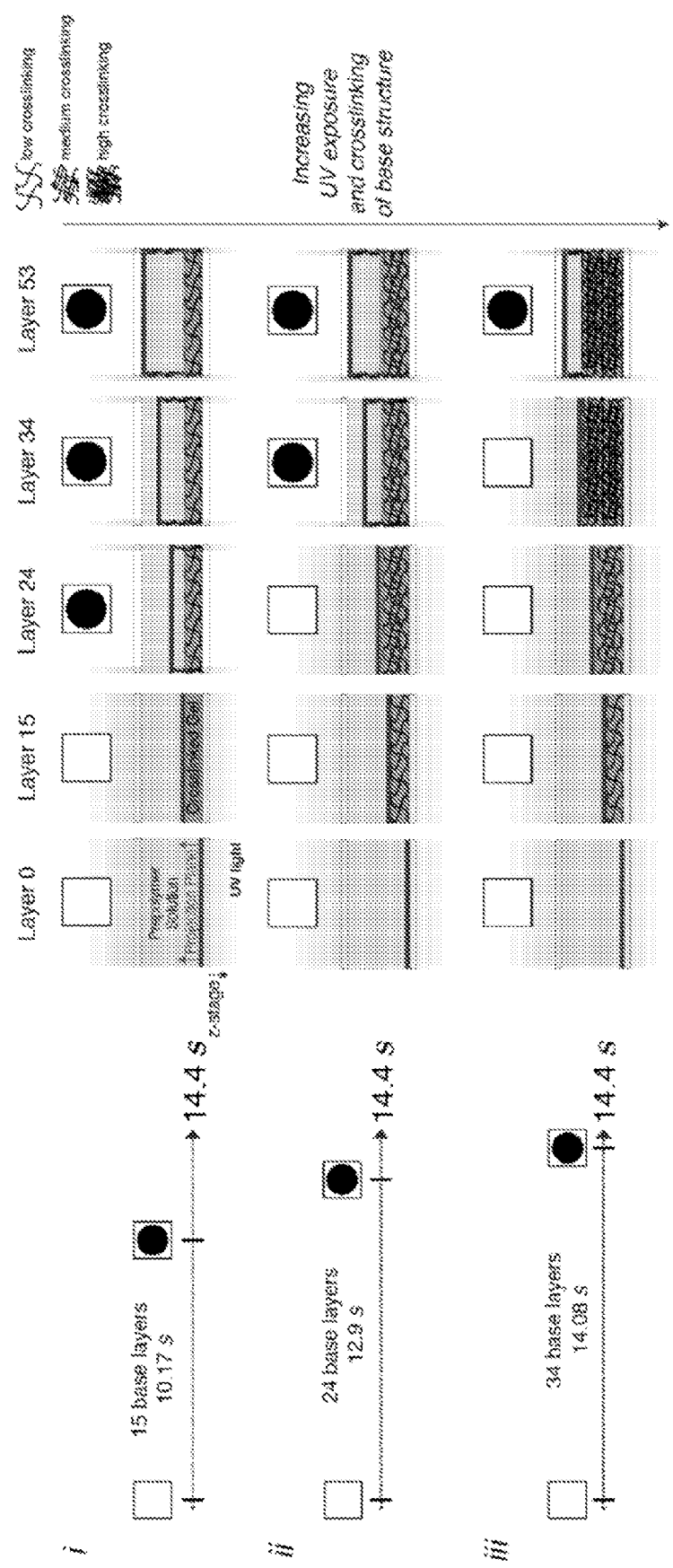
FIG. 2E schematically illustrates flat microwells exposed to different base layers in the nPOP process according to three scenarios for different base layers and exposure times.

As an extension of the platform's versatility in microwell design, we showed the fabrication of microwells with concave or flat shapes while maintaining the same fabrication parameters, but varying the number of layers in the base layer (15, 24 and 34), such that the total exposure time for the base layers—varied while the total exposure time remained constant at 14.4 seconds. Three different variations are illustrated in FIG. 2E. When used in cell culture, flat microwells formed several spheroids of varying sizes within each well, while concave microwells exhibited the desired single spheroid formation. This result is further illustrated in FIG. 2G, which compares two different gradient patterns against a flat pattern. The SEM micrographs in the second row show the microwells obtaining by printing the different patterns using the 3D printing platform while row three shows the resulting cell culture in the different shaped wells. (Scale bar=200 µm.)

Atomic force microscopy (AFM; MFP3D, Asylum Research) was used to assess the stiffness profile on the microwell surface of Gradient 1 (FIG. 2D). Briefly, a pyramidal probe, 0.08 N/m spring constant with a 35° half angle (PNP-TR20, Nanoworld), was used to indent the substrate. The probe indentation velocity was fixed at 2 µm/s with the trigger force of 2 nN. Elastic modulus maps were determined by the Hertz cone model with a sample Poisson ratio of 0.5 fit over a range of 10%-90% indentation force. AFM software (IGOR Pro 6.22 (WaveMetrics) was applied to generate the stiffness.

The microwell displayed a soft center (10 Pa) and stiffened to ~200 Pa on the edge of the well, before reaching the stiffer wall (~1-2 kPa). Values plotted in FIG. 2D are based on measurements taken at the points i-iv indicated in the SEM micrographs to the left of the plot, where i (center)=12 Pa; ii=48 Pa; iii=101 Pa; iv=2200 Pa. (Scale bars=200 µm.)

Figure 2F:
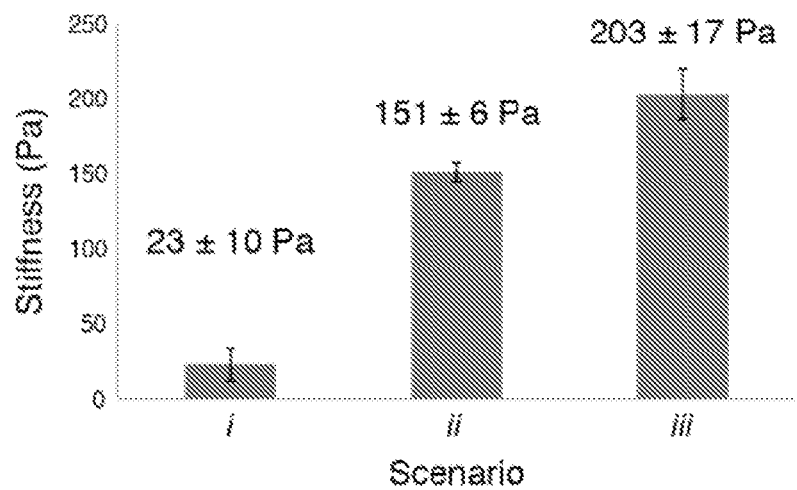
FIG. 2F plots the resulting stiffness profiles from atomic force microscopy measurements.
Figure 2G:
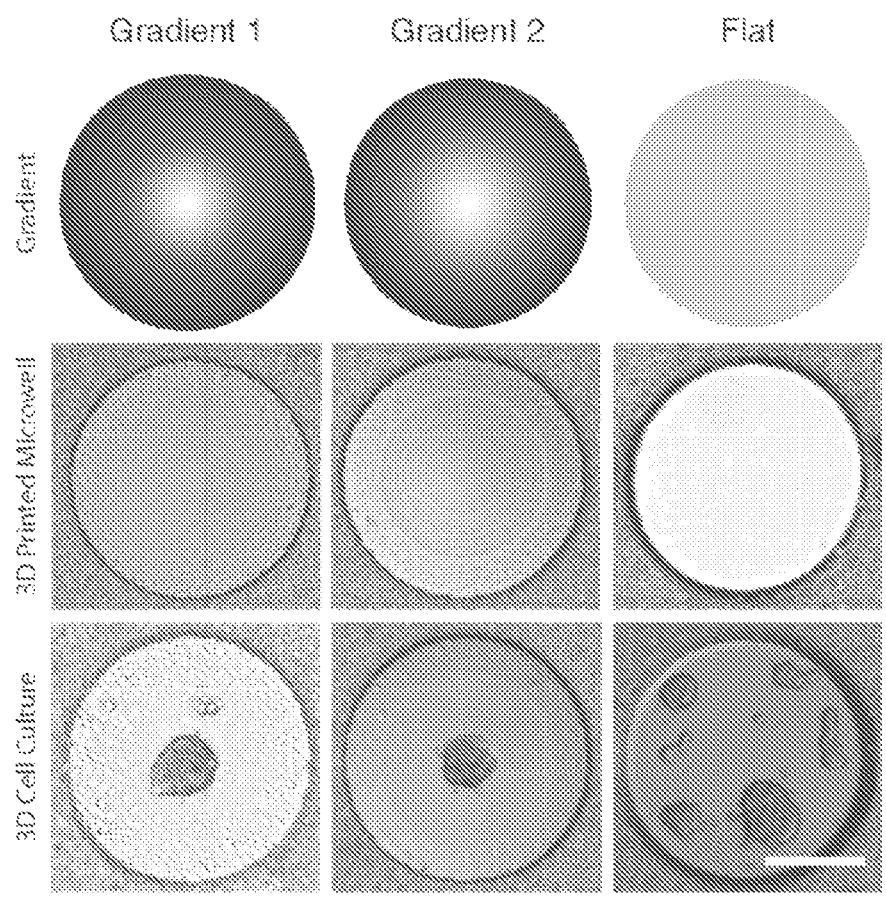
FIG. 2G illustrates two different exemplary gradient patterns compared to flat microwells. SEM images show the resulting 3D cell microwells and the 3D cell cultures (scale bar=200 μm).

We hypothesized that the soft center correlates to earlier layers of UV exposure during the fabrication process, and as it proceeds through the layers, increasing UV exposure drives additional crosslinking to stiffen the microwell. This was confirmed by taking stiffness measurements of flat microwells formed with different UV exposures to the base (according to FIG. 2E.) It appears that the flat wells with 15 base layers have an average stiffness of 20 Pa, while 24 base layers and 34 base layers have higher moduli profiles of 151 Pa and 203 Pa, respectively, as shown in FIG. 2F. Thus, it appears likely that the gradient UV exposure in the concave microwell is due to the variable light exposure in the layer-by-layer fabrication process. An advantage of the inventive platform is the ease with which the number of base layers can be changed in relation to the total number layers.

Figure 3A:
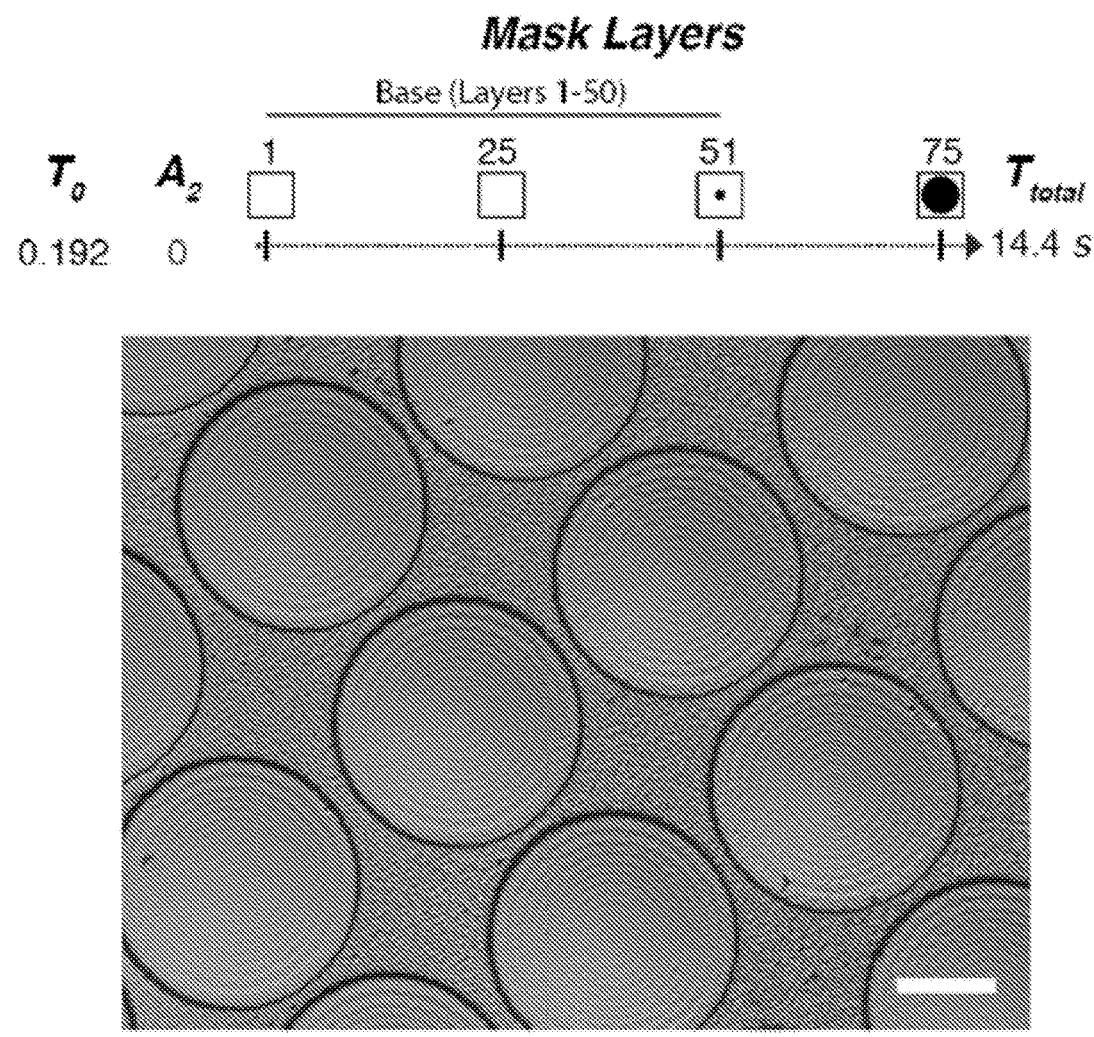
FIG. 3A schematically illustrates linear exposure optimized with baseline exposure values from FIGS. 2A and 2B with an SEM image of the resulting microwells (Scale bars=200 μm).

To evaluate whether non-linear exposure is, indeed, necessary to create the concave microwells useful for 3D cell culture, the same fabrication timeframe used for the aforementioned microwells was used in a non-linear exposure sequence: the total number of base layers were exposed for 10.2 seconds and the remaining layers were exposed for 4.2 seconds. For linear exposure of 75 total layers (50 base), this would require a $T_0$ value of 0.192 according to Equation 1 (and $A_2$=0). The exposure parameters and a SEM micrograph of the resulting microwells are shown in FIG. 3A.

Figure 3C:
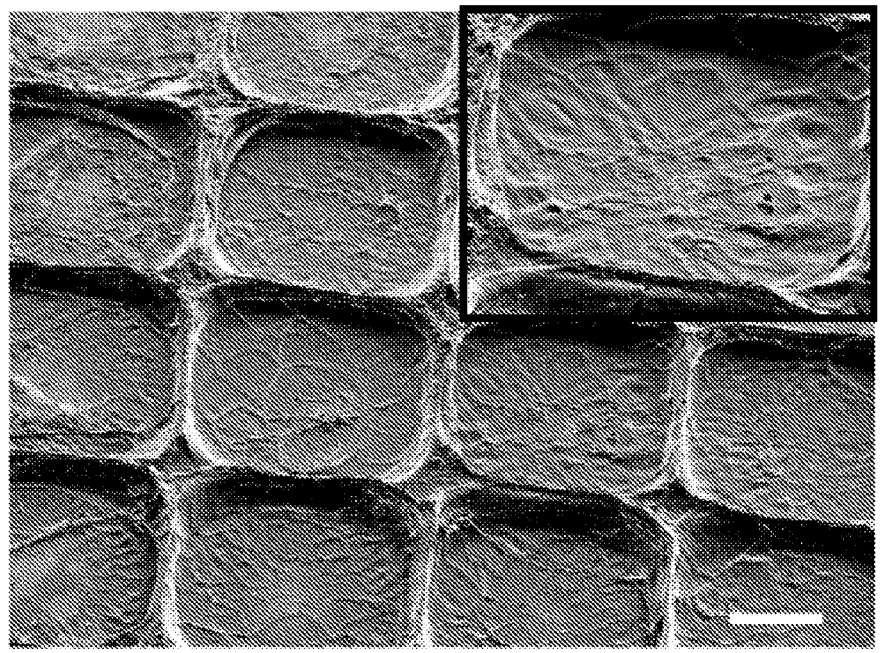
FIG. 3C is a SEM image of linear microwells, highlighting their relatively flat nature compared to nPOP microwells.

FIG. 3B is a plot showing the cumulative exposure time for the layers, comparing linear (L) and non-linear (NL) exposure processes. In the linear exposure setup, ~66% of the total layers are base layers (compared to just 28% for non-linear exposure). Because the stage moves in relation to the layers, a higher number of base layers in proportion to the total layers means that a smaller total movement in the z-direction is designated to the actual concave structure—and, we hypothesized this results in a flatter well. The SEM images shown in FIG. 3C (where the upper right corner inset is a single magnified well) confirm that microwells fabricated using linear exposure were indeed flatter in shape compared to non-linear ("nPOP") microwells.

Figure 3D:
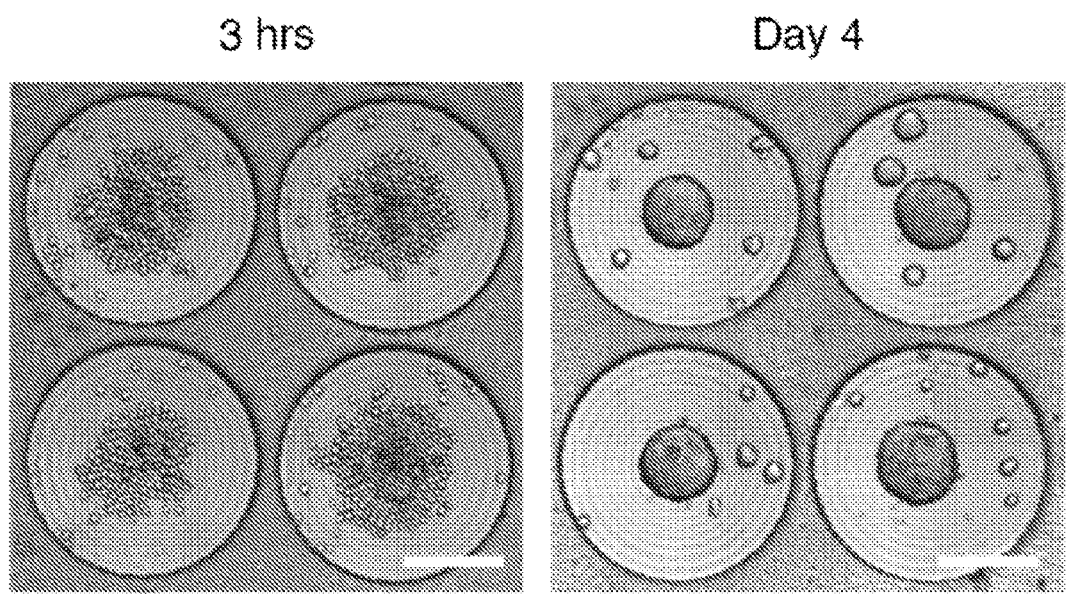
FIG. 3D provides SEM images of 3D cell spheroid culture within flat wells at 3 hours and at four days, showing a single large spheroid in the center and small satellite cell clusters on the periphery of the wells.

FIG. 3D provides SEM micrographs of cell culture tests with BT474 cells, after 3 hours (left) and 4 days (right), showing that the flatter wells fabricated under these conditions resulted in the formation of one large spheroid in the middle of each well and more cell clusters on the periphery of the wells, presumably due to their flat nature. These results suggest that non-linear exposure is preferred, and possibly necessary, for creating a more concave shape for spheroid generation compared to linear exposure. Further, this reaffirms that baseline exposure is a key factor in maintaining structural integrity of the microwell. For the remaining experiments, we chose to explore the utility of our microwells fabricated with non-linear exposure in 3D cell culture.

Figure 4A:
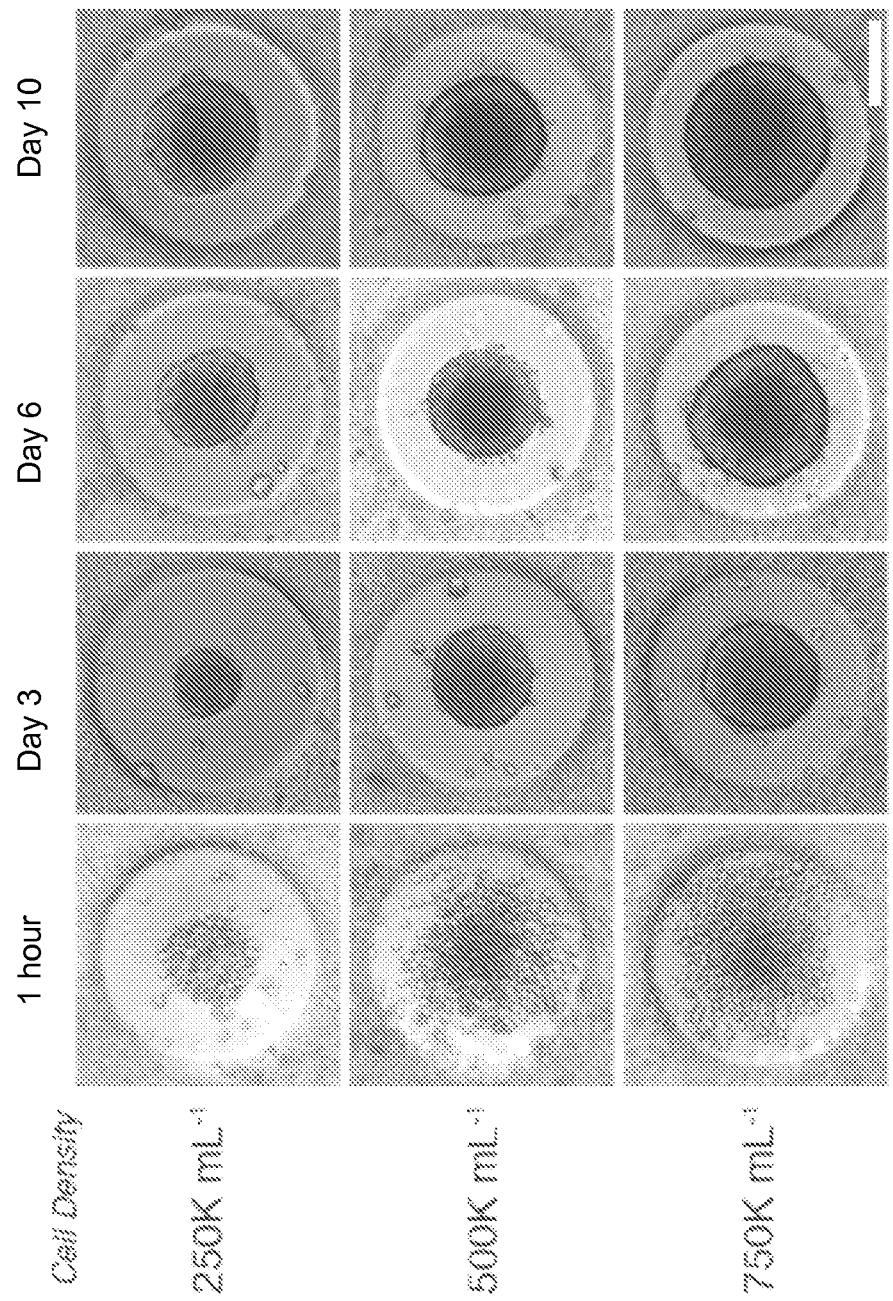
FIG. 4A-4B illustrate examples of how nPOP microwells drive formation and allow for the growth of BT474 tumor spheroids, where FIG. 4A provides timelapse images of spheroids grown at densities 250, 500, and 750K cells mL$^{-1}$.

Expanding on the initial cell experiments, BT474 breast cancer cells were seeded at various densities and used to assess spheroid generation and growth within the microwells, as shown in the SEM images of FIG. 4A (scale bar=200 µm). BT474 cells were obtained from ATCC and were maintained in RPMI-1640 media supplemented with 10% (v/v) fetal bovine serum (FBS), penicillin/streptomycin/L-glutamine, and Fungizone (Omega Scientific Inc.). Microwells were sterilized under UV light, and BT474 cells were seeded into the wells at the concentrations of 250 k $mL^{-1}$, 500 k $mL^{-1}$, and 750 k $mL^{-1}$.

Figure 4B:
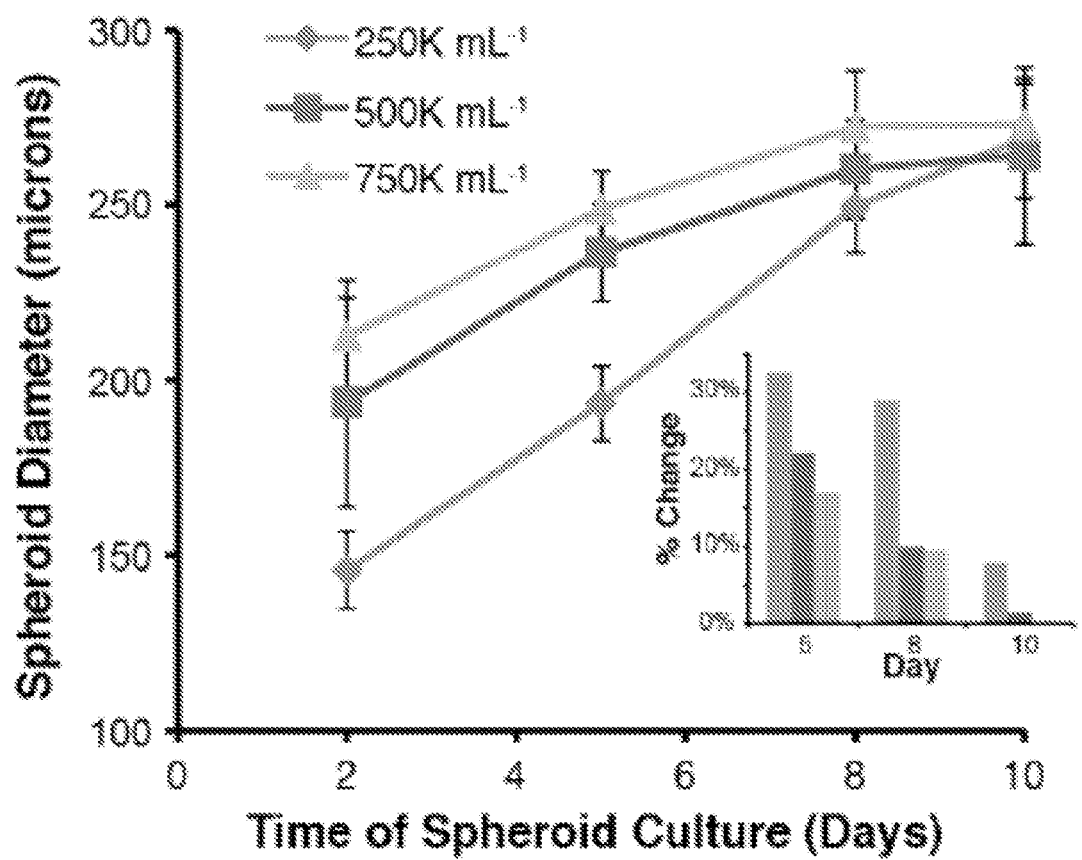

At day 2, cell seeding densities of 250 k, 500 k, and 750 k cells $mL^{-1}$ produced spheroids with diameters 146±11 µm, 194±30 µm, and 213±16 µm, respectively (FIG. 4B). Brightfield images of cancer spheroids were taken at various time points using a Leica Fluorescence Microscope, and a live/dead fluorescence assay (calcein AM/ethidium homodimer) was performed at day 10 to qualitatively assess cell viability. Spheroid size was quantified using ImageJ software. Spheroids also grown to day 10 were fixed in 4% paraformaldehyde and cryosectioned at 20 µm thickness. Sections were stained for Hif-1α (1:50 HIF-1α mouse mAb, Novus Biologicals), a hypoxia marker, and DAPI, a nuclear stain, and H&E staining was also performed.

Over the course of several days following seeding, spheroids from the higher cell densities began to plateau at a size of around 250-275 µm, while the smaller spheroids with an initial density of 250 k $mL^{-1}$ continued to grow in size, albeit smaller than the 250 µm threshold. Growth rates for each group confirmed this trend, as shown in the inset in FIG. 4B. Darkening, a possible visual marker for necrosis or hypoxia, was observed in the core of the spheroid beyond this plateau.

At day 10, spheroid diameters for all three groups were within standard deviations of each other (269±17 µm, 264±25 µm, 273±12 µm for 250, 500, and 750 k $mL^{-1}$ cell densities respectively).

Figure 4C:
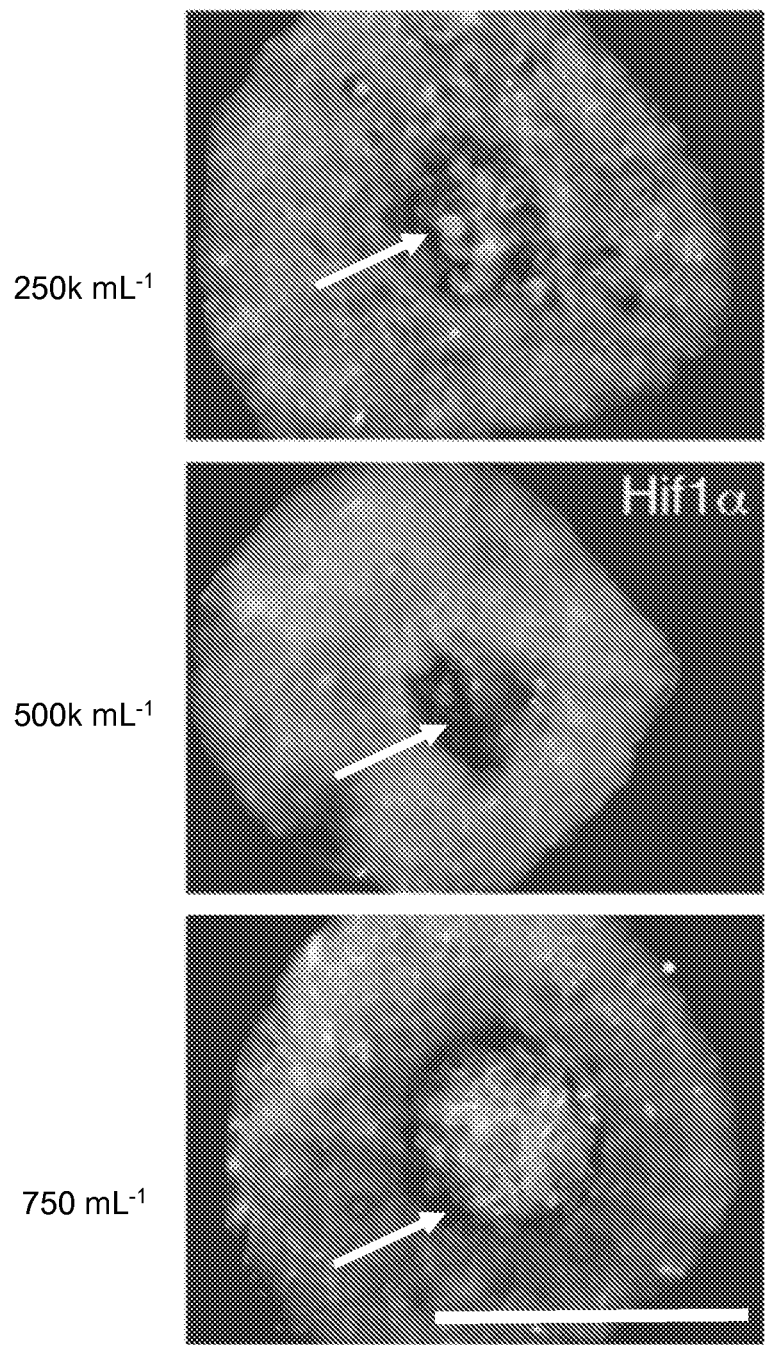
FIG. 4C is a set of SEM micrographs of immunohistochemistry staining of HIF-1-alpha (hypoxia marker) of spheroid cross-sections for the different seeding densities (scale bars=200 μm.)
Figure 4D:
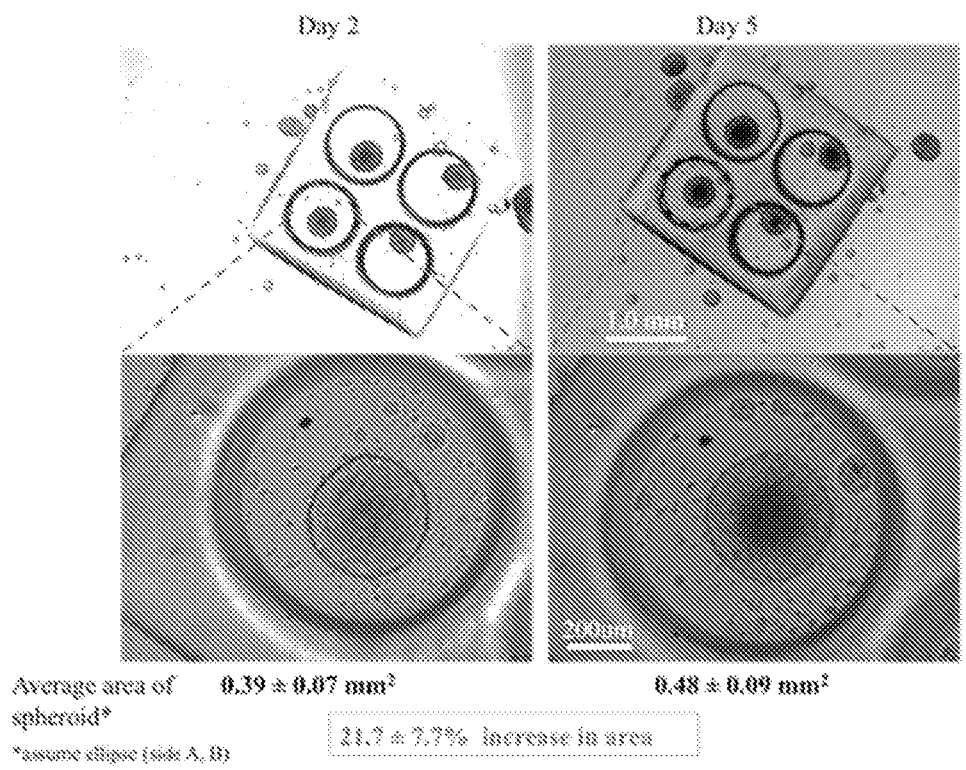
FIG. 4D is a set of SEM micrographs showing tumor cells at two different time points to demonstrate cell growth (scale bars=1.0 mm (upper) and 200 μm (lower).)

Interestingly, live/dead staining with calcein AM/ethidium homodimer showed considerable cell death in the 500 and 750 K $mL^{-1}$ seeding densities compared to the lower 250 K $mL^{-1}$ at day 10. This observation could be indicative of a necrotic core forming for these initially larger spheroids, correlating with regression in spheroid growth. It has been well documented that tumor spheroids greater than ~200 µm in diameter demonstrate a hypoxic core due to a nutrient and gas transport gradient, which in turn can lead to necrosis. The presence of a hypoxic core in the tumor spheroid provides a more physiologically relevant tumor model for cancer screening applications, since tumor hypoxia in vivo often drives angiogenesis. Hypoxia was confirmed with immunostaining of the spheroid cross-sections using HIF-1α, a biomarker for hypoxia (FIG. 4C). Necrosis was observed in hematoxylin and eosin staining. The spheroids showed considerable hypoxia and necrosis more prevalently in spheroids of higher cell seeding densities. FIG. 4D provides another illustration of the effectiveness of cell culture using microwells fabricated using the inventive nPOP platform. Cancer tumor cells are shown at two different time points to demonstrate cell growth, increasing from average size 0.39±0.07 $mm^2$ at day 2 to 0.48±0.09 $mm^2$ at day 5, representing a 21.7±7.7% increase in area over 3 days. As further indication of the utility of this approach and its effectiveness in simulating in vivo tumor growth, a dark necrotic/hypoxic core can be seen in the day 5 "micro-tumor."

The foregoing data are in good agreement with previous literature regarding tumor spheroid progression (e.g., hypoxia and necrosis). Furthermore, they support our earlier observation that cell death increases with increasing cell seeding densities.

Referring to FIGS. 5A-5D, human induced pluripotent stem cells (iPSCs) were also used to further validate the 3D printed microwell platform in generating embryoid bodies (EBs). iPSCs, derived by retroviral transduction of a combination of four transcription factors, Oct4, Sox2, c-Myc and Klf4, are stem cells with an equivalent self-renewal and differentiation capacity as embryonic stem cells. In addition to their pluripotency, iPSCs provide a superior platform for clinical translation because they are autologous by nature (patient-specific). This facilitates their use in personalized disease modeling, drug testing, and regenerative medicine development, as well as minimizing any ethical concerns.

Human perinatal foreskin fibroblasts (BJ, ATCC) and human adult dermal fibroblasts (HDF, Cell Applications) were maintained in DMEM (Corning) supplemented with 10% Fetal Bovine Serum (Tissue Culture Biologicals) and Antibiotics/Antimicotic (Corning) in a 37° C., 5% $CO_2$ incubator. Cells were passaged at a ratio of 1:6 every 3-5 days by 0.25% Trypsin-EDTA (Corning) before reprogramming $T_0$ prepare for reprogramming, fibroblasts were seeded at a density of $2\times10^5$ cells/well in 6-well plates, and allowed to attach and spread for 48 h. Reprogramming was performed following the instructions in a Sendai virus-based CYTOTUNE® iPS reprogramming kit (Life Technologies) for the delivery of four factors Oct4, Sox2, Klf4 and c-Myc.

Following successful reprogramming, growth factor reduced MATRIGEL® (BD Biosciences, N.J., USA) was used as the substrate for the maintenance of the iPSCs culture in serum- and feeder-free conditioned medium (StemPro®, Life Technologies) following the manufacturer's instructions. Cells were split at a ratio of 1:6 every 3-4 days by VERSENE® (Life Technologies) before experiments.

Similar to the cancer cell seeding protocol, microwells were sterilized under UV irradiation for 1 hour. Human iPSCs at 70-80% confluency were detached by ACCUTASE® cell detachment solution (Innovative Cell Technologies) and re-suspended in regular culture medium with 5 uM ROCK (Rho-associated kinase) inhibitor Y27632 (STEMGENT®). Cells were seeded at a concentration of 100 k or 400 k per milliliter into each of the well with microwell construct. The plates were spun at a speed of 210 rcf for 5 minutes and then incubated in a 37° C., 5% $CO_2$ incubator for 24 hours. Maintenance medium was replaced every day.

iPSCs were seeded on top of the microwells at varying cell densities (either 100 k or 400 k cells $mL^{-1}$) and imaged over three days. Embryoid bodies (EBs) were fixed in 4% paraformaldehyde in PBS three days following seeding. They were subsequently permeabilized with 0.1% Triton X-100 in PBS and incubated with antibodies against Oct4 (Cell Signaling Technology) and Nanog (Cell Signaling Technology) followed by fluorophore-conjugated anti-IgG antibodies. DAPI (Invitrogen) nucleus counterstain was also performed. For differentiation studies, EBs were grown in the same manner in the inventive microwells at varying concentrations (100 k or 400 k cells $mL^{-1}$) for 10 days, followed by fixing and immunostaining with biomarkers for the three germ layers: SOX-1 for ectoderm, SOX-17 for endoderm, and Brachyury for mesoderm (R&D Systems). Images were taken using a Leica fluorescence microscope and an Olympus confocal microscope.

Figure 5A:
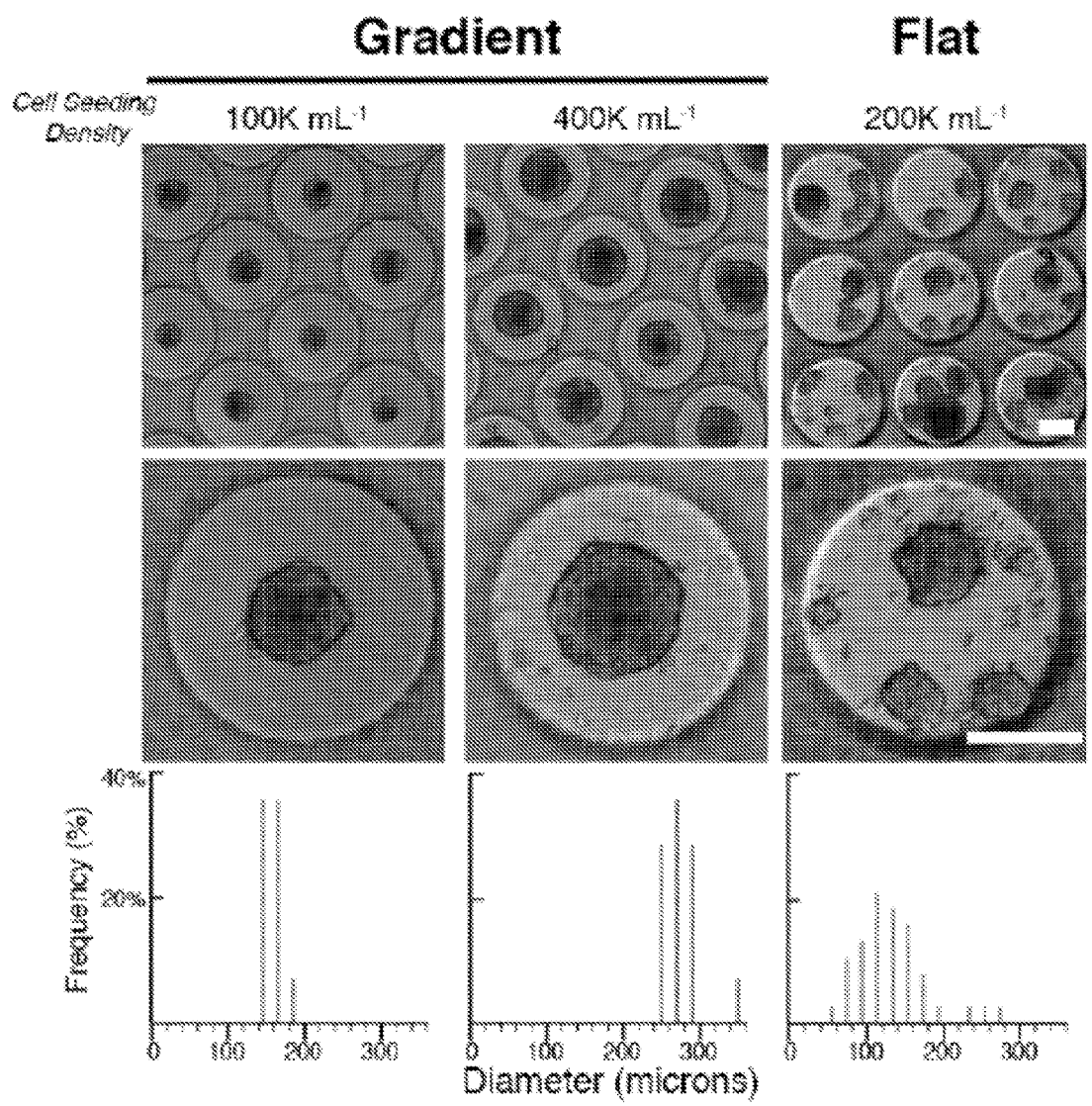
FIG. 5A is a set of SEM micrographs showing H-iPSCs grown on either concave or flat microwells at varying cell seeding concentrations. The plots are the bottom of the figure show accompanying size distribution of EBs (n=at least 14 for each group) (scale bars=200 μm).
Figure 5B:
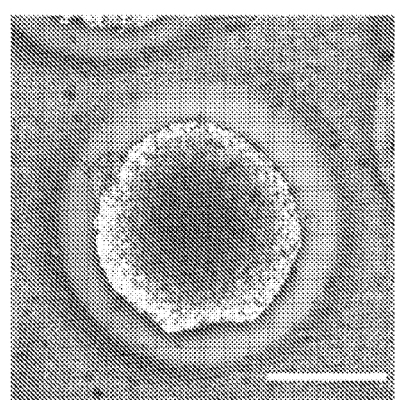
FIG. 5B is a SEM micrograph showing immunofluorescent staining of EBs grown in the concave microwells with Nanog, a marker for pluripotency (scale bar=200 μm).

Single EBs could be formed in the concave wells after three days in proportion to the seeding density (FIG. 5A, left and center columns). Flat microwells, shown in the right column of FIG. 5A, conversely, generated a heterogeneous population of EB sizes, a phenomenon previously observed with the BT474 breast cancer cell line, as indicated by the frequency plot in each column. This is also consistent with previous reports of flat microwells, where it has been established that EBs only form at a critical cell density proportional to the microwell size, below which they form infrequently or at varied sizes. Size distributions are also reported. Non-linear concave microwells seeded with 100 K cells $mL^{-1}$ and 400 K cells $mL^{-1}$ produced EBs of 155±17 μm and 274±20 μm, respectively, while flat microwells seeded with 200 K cells $mL^{-1}$ showed a much broader distribution of sizes, with an average size of 129±48 μm. EBs were fixed and immunostained for Nanog and Oct4, transcription factors highly expressed in embryonic stem cells and key markers of pluripotency. FIG. 5B shows the results for the Nanog-stained EBs. Similar expression patterns of these markers could be observed in all cases (e.g., concave and flat); however, only the concave microwells gave rise to EBs of uniform size.

Figure 5C:
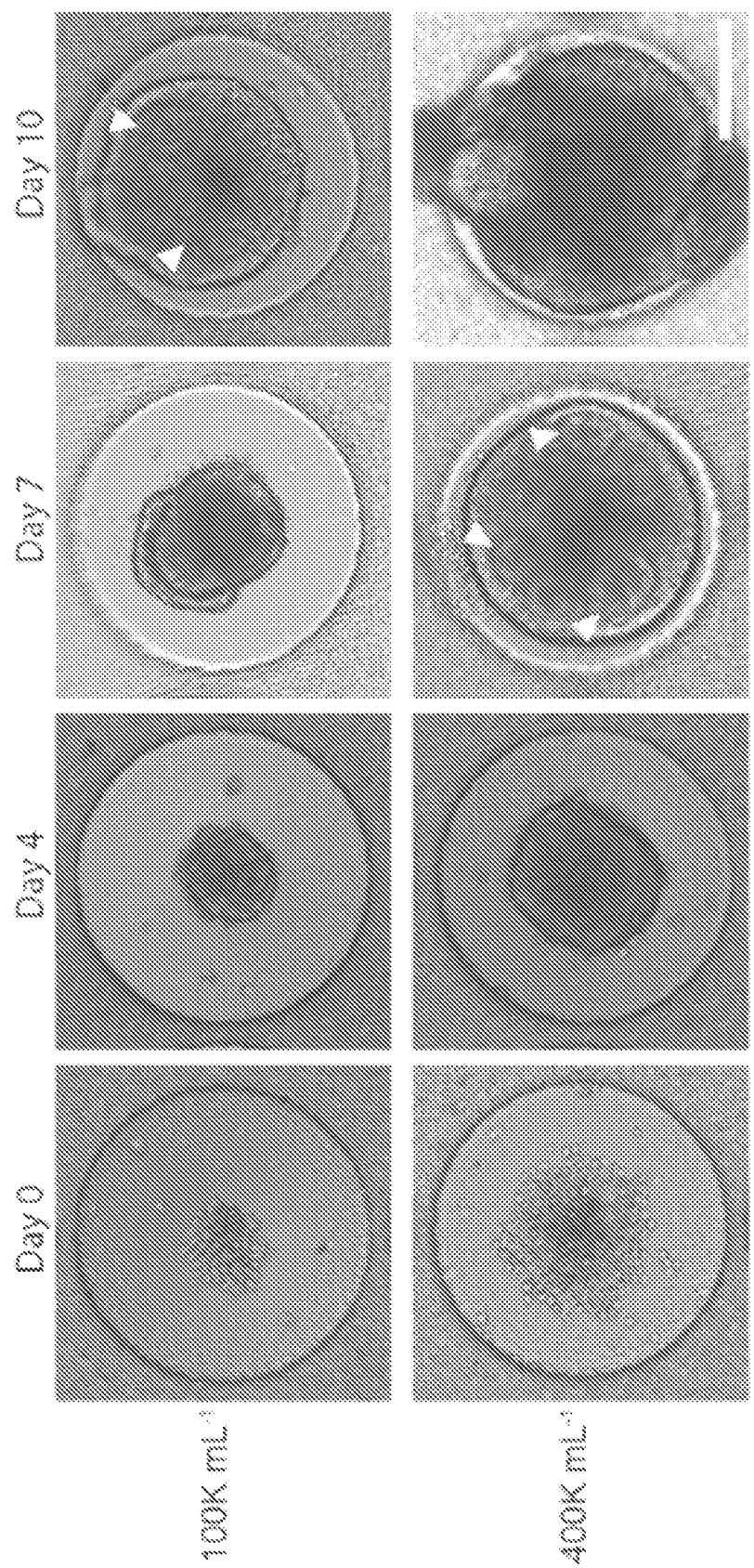
FIG. 5C is a set of SEM micrographs showing morphological changes to EBs over time at different initial cell seeding densities. Arrows indicate regions of intraorganoid cavities forming (scale bars=200 μm).
Figure 6:
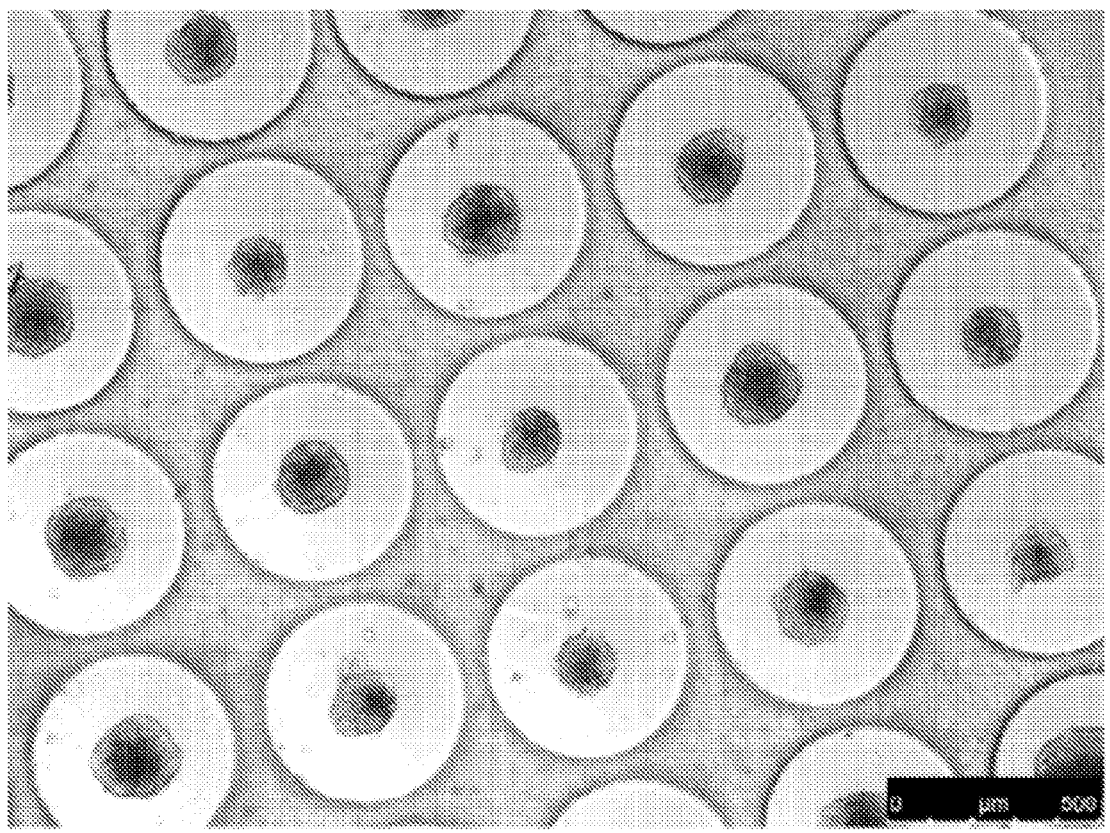
FIG. 6 is a SEM micrograph illustrating 100 K mL$^{-1}$ cell seeding of induced pluripotent stem cells in the microwells at day 3 (scale bar=500 μM.)

At day 10, EBs displayed morphological changes in their size, shape, and appearance in the form of intra-organoid cavities, as shown in FIG. 5C. The white arrows indicate regions of intraorganoid cavities forming. We hypothesized that this was due to the spontaneous differentiation that occurs in these pluripotent cells, based on similar observations in the literature. Immunostaining for the three germ layers confirmed EB differentiation to all three germ layers as evidenced by their co-expression of SOX-17 (endoderm), SOX-1 (ectoderm) and brachyury (mesoderm). FIG. 6 is a SEM showing 100 k $mL^{-1}$ seeding of induced pluripotent stem cells at day 3 in an array of microwells fabricated according to an embodiment of the inventive nPOP technology. This provides a clear demonstration of the high degree of uniformity in both formation and positioning of the spheroid formation.

Figure 7A:
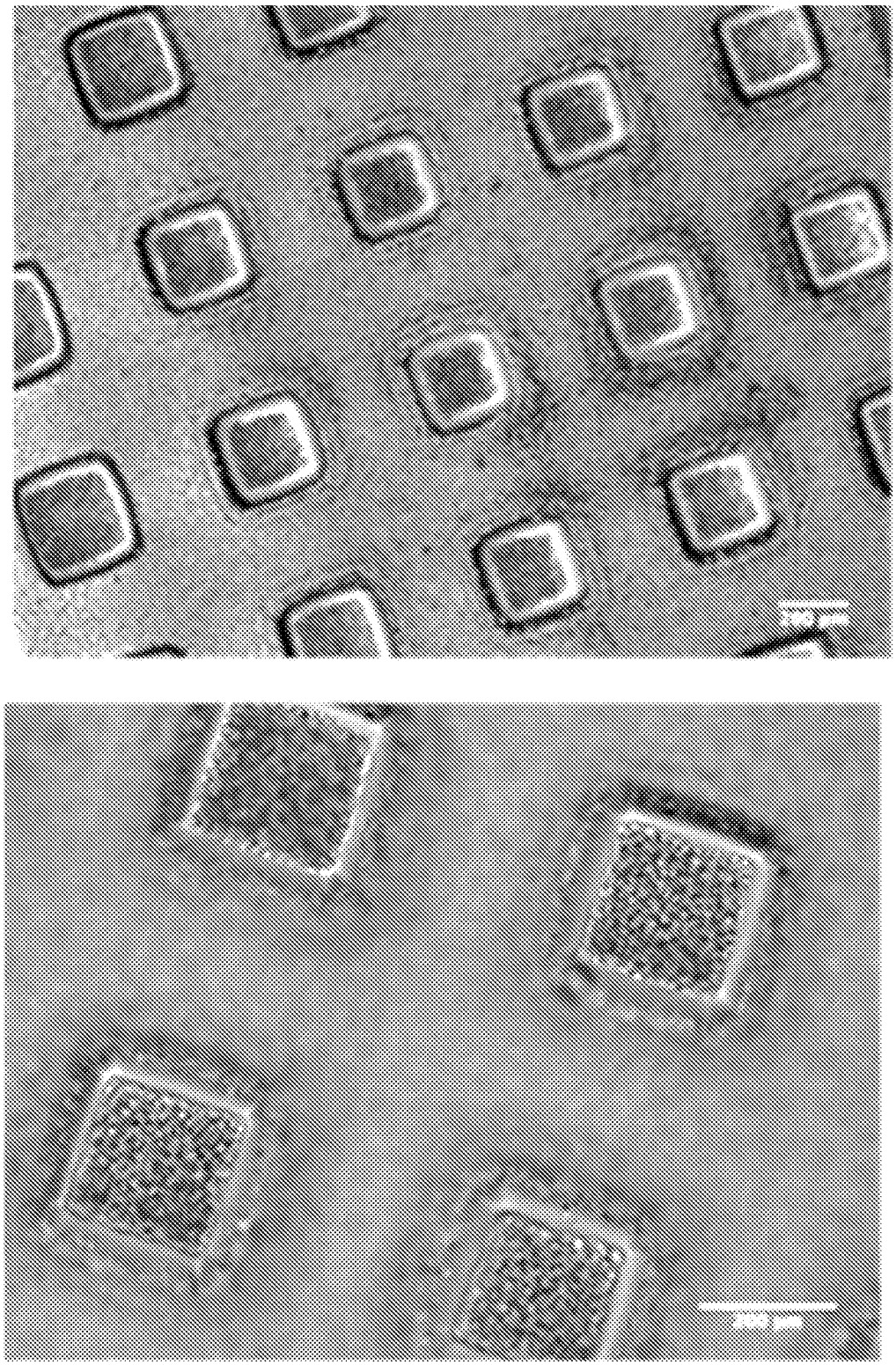
FIGS. 7A-7C are brightfield images (5x) of PSCs cultured in the square, circular and annular microwells of 500 μm depth, respectively. (All scale bars=200 μm.)
Figure 7B:
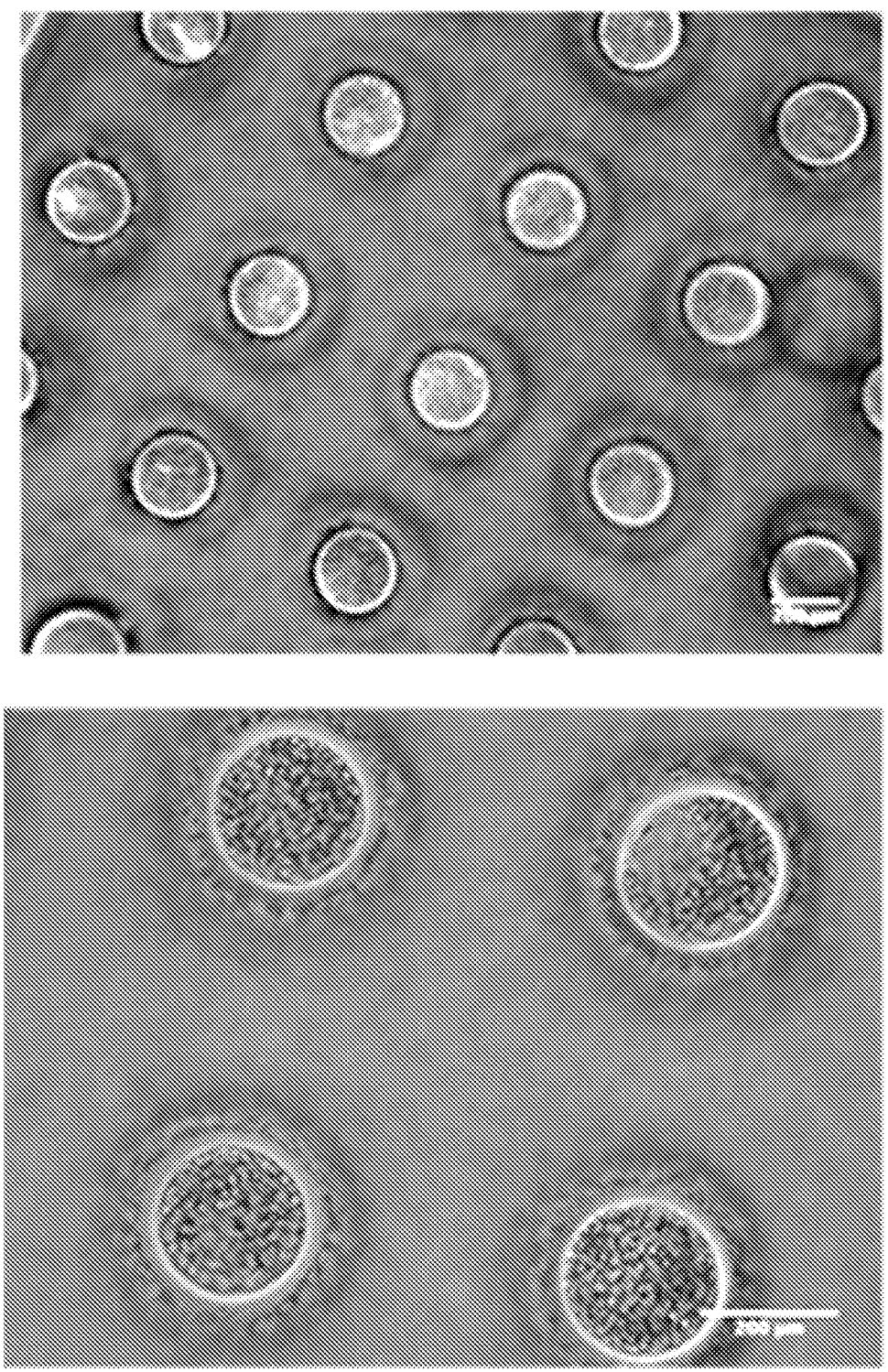
Figure 7C:
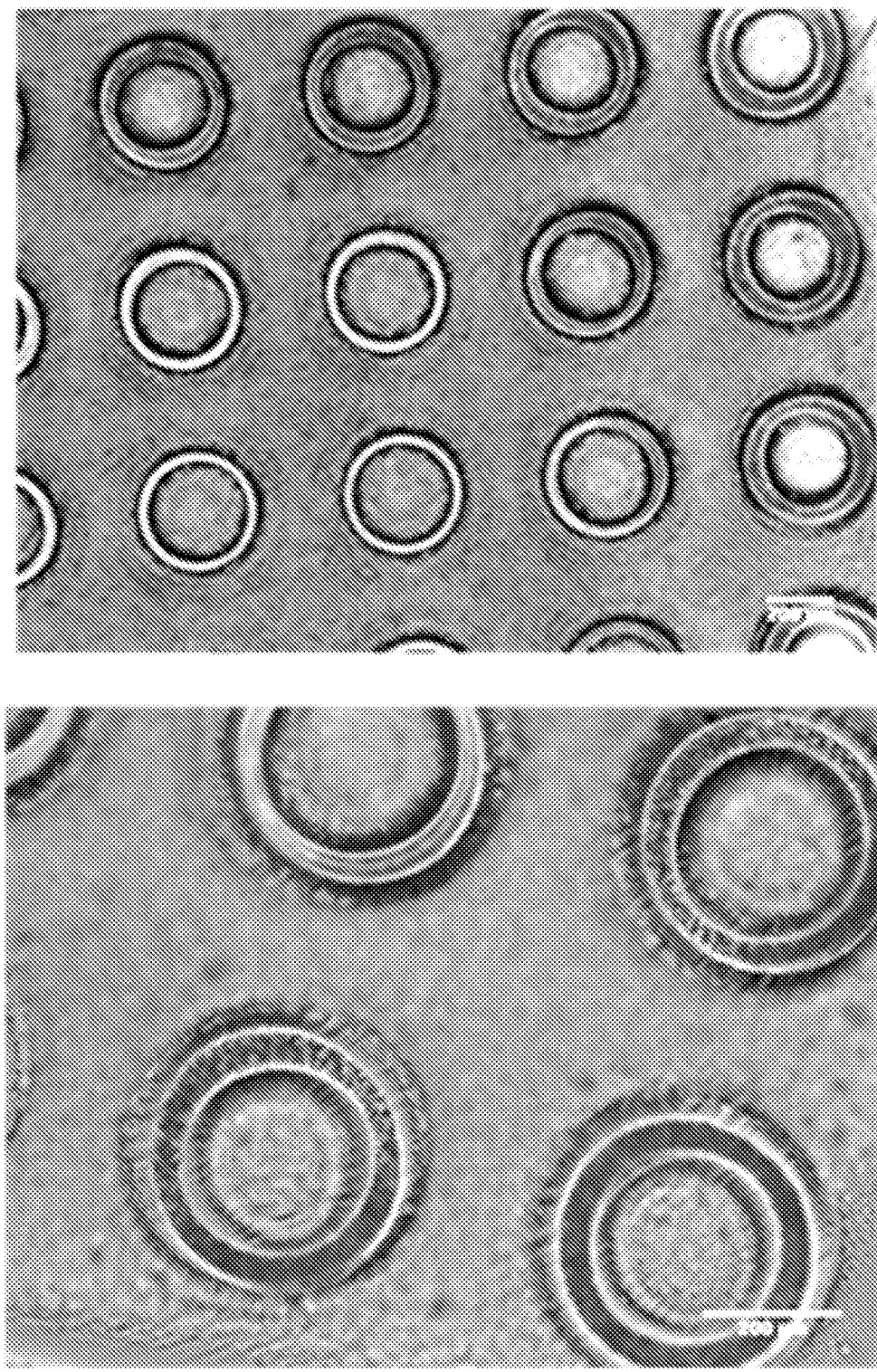

Using the inventive non-linear projection optical printing (nPOP) technology, microwells of various sizes and shapes were developed to control the 3D PSC aggregate shapes in vitro. Microwells of circular, square and ring shapes of 500 μm in thickness were printed using the nPOP platform for controlling aggregation of both human induced pluripotent stem cells (iPSCs) and mouse embryonic stem cells. As shown in the brightfield images of FIGS. 7A-7C, PSCs in the square, circular and annular microwells, respectively, adapted to the shapes of the wells and can be expected to develop polarity in their aggregates. The ability to control 3D shapes of PSC aggregates provides a powerful tool for the study of embryogenesis and, potentially, for prenatal drug screening.

Based on these results, the nPOP technology can facilitate EB formation and culture maintenance, demonstrating pluripotency at early time points as well as differentiation at later time points, making it a potential tool for understanding early embryonic development at large.

3D cell culture has a high potential to improve drug screening validation practices and enhance tissue engineering and stem cell fields, however the current methodologies for cluster generation are labor intensive, sometimes non-optically clear, uncontrolled, or require plate transfer. There is thus, a pressing need to create reproducibly sized spheroids on an optically-clear, non-adhering, low protein absorption substrate for the formation of multicellular clusters.

The PEG microwells fabricated using the nPOP printing methods described herein provide the precisely controlled concavities needed for controlled cell culture. These microwells represent a significant enhancement over current technologies that often require spheroid transfer upon formation and full saturation of the wells. This novel approach will enable others to perform various 3D cellular assays with controlled ease of growing and maintaining spheroids without the need for spheroid transfer, and can greatly impact drug screening, tissue engineering and the 3D bioprinting fields in general. Furthermore, the ability to generate consistently sized tumors of physiologically relevant sizes (greater than >600 microns in diameter), opens the door to exploring more fundamental cancer biology questions, such as migration and metastasis.

The following publications are incorporated herein by reference to the extent that they teach the general state of the art to facilitate understanding of the present invention:
1. Derby, B., "Printing and prototyping of tissues and scaffolds," *Science* 338, 921-926 (2012).
2. Ungrin, M. D., Joshi, C., Nica, A., Bauwens, C. & Zandstra, P. W. "Reproducible, ultra high-throughput formation of multicellular organization from single cell suspension-derived human embryonic stem cell aggregates," *PloS One* 3, e1565 (2008).
3. Huh, D., Hamilton, G. A. & Ingber, D. E., "From 3D cell culture to organs-on-chips," *Trends in Cell Biology* 21, 745-754 (2011).
4. Lee, M. Y. et al., "Three-dimensional cellular microarray for high-throughput toxicology assays," *PNAS* 105, 59-63 (2008).
5. Elliott, N. T. & Yuan, F., "A review of three-dimensional in vitro tissue models for drug discovery and transport studies," *J. Pharmaceutical Sciences* 100, 59-74 (2011).

6. Pampaloni, F., Reynaud, E. G. & Stelzer, E. H., "The third dimension bridges the gap between cell culture and live tissue," *Nature Reviews Molecular Cell Biology* 8, 839-845 (2007).
7. Hribar, K. C., Soman, P., Warner, J., Chung, P. & Chen, S., "Light-assisted direct-write of 3D functional biomaterials," *Lab on a Chip* 14, 268-275 (2014).
8. Debnath, J. & Brugge, J. S., "Modelling glandular epithelial cancers in three-dimensional cultures," *Nature Reviews Cancer* 5, 675-688 (2005).
9. Karp, J. M. et al., "Controlling size, shape and homogeneity of embryoid bodies using poly(ethylene glycol) microwells," *Lab on a Chip* 7, 786-794 (2007).
10. Hwang, Y. S. et al., "Microwell-mediated control of embryoid body size regulates embryonic stem cell fate via differential expression of WNTSa and WNT11," *PNAS* 106, 16978-16983 (2009).
11. Choi, Y. Y. et al., "Controlled-size embryoid body formation in concave microwell arrays," *Biomaterials* 31, 4296-4303 (2010).
12. Itskovitz-Eldor, J. et al., "Differentiation of human embryonic stem cells into embryoid bodies compromising the three embryonic germ layers," *Molecular Medicine* 6, 88-95 (2000).
13. Spence, J. R. et al., "Directed differentiation of human pluripotent stem cells into intestinal tissue in vitro," *Nature* 470, 105-109 (2011).
14. Laib, A. M. et al., "Spheroid-based human endothelial cell microvessel formation in vivo," *Nature Protocols* 4, 1202-1215 (2009).
15. Kelm, J. M. et al., "Design of custom-shaped vascularized tissues using microtissue spheroids as minimal building units," *Tissue engineering* 12, 2151-2160 (2006).
16. Friedrich, J., Seidel, C., Ebner, R. & Kunz-Schughart, L. A., "Spheroid-based drug screen: considerations and practical approach," *Nature Protocols* 4, 309-324 (2009).
17. Hirschhaeuser, F. et al., "Multicellular tumor spheroids: an underestimated tool is catching up again," *J. Biotechnology* 148, 3-15 (2010).
18. Kunz-Schughart, L. A., Freyer, J. P., Hofstaedter, F. & Ebner, R., "The use of 3-D cultures for high-throughput screening: the multicellular spheroid model," *J. Biomolecular Screening* 9, 273-285 (2004).
19. Fukuda, J. & Nakazawa, K., "Orderly arrangement of hepatocyte spheroids on a microfabricated chip. *Tissue engineering* 11, 1254-1262 (2005).
20. Thoma, C. R. et al. A high-throughput-compatible 3D microtissue co-culture system for phenotypic RNAi screening applications," *J. Biomolecular Screening* 18, 1330-1337 (2013).
21. Moeller, H. C., Mian, M. K., Shrivastava, S., Chung, B. G. & Khademhosseini, A., "A microwell array system for stem cell culture," *Biomaterials* 29, 752-763 (2008).
22. Toepke, M. W. & Beebe, D. J., "PDMS absorption of small molecules and consequences in microfluidic applications," *Lab on a Chip* 6, 1484-1486 (2006).
23. Peppas, N. A., Hilt, J. Z., Khademhosseini, A. & Langer, R., "Hydrogels in Biology and Medicine: From Molecular Principles to Biotechnology," *Adv. Mater.* 18, 1345-1360 (2006).
24. Kizilel, S., Perez-Luna, V. H. & Teymour, F., "Mathematical model for surface-initiated photopolymerization of poly(ethylene glycol) diacrylate," *Macromol. Theor. Simul* 15, 686-700 (2006).
25. Takahashi, K. et al., "Induction of pluripotent stem cells from adult human fibroblasts by defined factors," *Cell* 131, 861-872 (2007).
26. Choi, Y. S. et al., "The alignment and fusion assembly of adipose-derived stem cells on mechanically patterned matrices," *Biomaterials* 33, 6943-6951 (2012).
27. Radmacher, M., "Studying the mechanics of cellular processes by atomic force microscopy," *Method Cell Biol* 83, 347-372 (2007).

The invention claimed is:

1. A method for three-dimensional printing of a concave structure, comprising:
    providing a plurality of masks, each mask representing a cross-section of a layer of the concave structure; and
    progressively moving a projection plane to expose a pre-polymer solution to a polymerizing radiation source modulated by the plurality of masks to define the plurality of layers of the concave structure, wherein each layer is exposed for an exposure period within a total exposure time, wherein the exposure periods are non-equal portions of the total exposure time, wherein a first portion of the plurality of masks comprises base layer masks, wherein a first exposure period for the first portion is longer than subsequent exposure periods, and wherein the total exposure time is determined according to the relationship $T_0+T_0*(1+L_i*A_2)^2$, where $T_0$ is the first exposure period, $L_i$ is a layer number of a layer of the plurality of layers, and $A_2$ is a non-linear factor.

2. The method of claim 1, wherein the non-linear factor $A_2$ is within a range of −0.025 to 0.

3. The method of claim 1, wherein the first exposure period $T_0$ is within a range of 0.5 second to 1 second.

4. The method of claim 1, wherein the non-linear factor $A_2$ is −0.023 and the first exposure period $T_0$ is 0.95.

5. The method of claim 1, wherein the total exposure time is within a range of 10 seconds to 30 seconds.

6. The method of claim 1, wherein the pre-polymer solution is PEGDA.

7. The method of claim 1, wherein the step of progressively moving comprises moving a stage supporting a container containing the pre-polymer solution along a z-axis relative to the polymerizing radiation source.

8. The method of claim 1, wherein the stage is moved at non-equal time increments corresponding to the exposure periods.

9. The method of claim 1, wherein the plurality of masks is configured for defining an array of circular patterns of progressively increasing diameter from a bottom of the concave structure to a top of the concave structure.

10. The method of claim 1, wherein a first portion of the plurality of masks comprises no pattern, so that the entire pre-polymer solution is exposed to polymerizing radiation.

11. The method of claim 1, wherein the concave structure has a shape selected from circular, oval, square, rectangular, annular, polygonal, and other geometric shapes.

12. The method of claim 1, wherein the concave structure is optically clear.

13. A method for three-dimensional printing of a concave structure, comprising:
    providing a plurality of masks configured for modulating a polymerizing radiation source to project an array of patterns of progressively increasing diameter to define layers of the concave structure; and
    progressively moving a projection plane to expose a pre-polymer solution to the modulated polymerizing radiation source to define the layers, wherein each layer is exposed for an exposure period within a total exposure time, wherein the exposure periods are non-equal portions of the total exposure time, wherein a first portion of the plurality of masks comprises base layer masks, wherein a first exposure period for the first portion is longer than subsequent exposure periods, and wherein the total exposure time is determined according to the relationship $T_0+T_0*(1+L_i*A_2)^2$, where $T_0$ is the first exposure period, $L_i$ is a layer number, and $A_2$ is a non-linear factor.

14. The method of claim 13, wherein the non-linear factor $A_2$ is within a range of −0.025 to 0.

15. The method of claim 13, wherein the first exposure period $T_0$ is within a range of 0.5 second to 1 second.

16. The method of claim 13, wherein the pre-polymer solution is PEGDA.

17. The method of claim 13, wherein the step of progressively moving comprises moving a stage supporting a container containing the pre-polymer solution along a z-axis relative to the polymerizing radiation source.

18. The method of claim 13, wherein the stage is moved at non-equal time increments corresponding to the exposure periods.

19. The method of claim 13, wherein the concave structure is optically clear.

20. The method of claim 13, wherein each pattern of the array of patterns has a shape selected from circular, oval, square, rectangular, annular, polygonal, and other geometric shapes.

* * * * *